US009835559B2

(12) United States Patent
Ozasa et al.

(10) Patent No.: US 9,835,559 B2
(45) Date of Patent: Dec. 5, 2017

(54) URINE SPECIMEN ANALYSIS DEVICE AND URINE SPECIMEN ANALYSIS METHOD

(71) Applicant: Sysmex Corporation, Kobe-shi, Hyogo (JP)

(72) Inventors: Masatsugu Ozasa, Kobe (JP); Kanako Nagaoka, Kobe (JP); Akinori Kawai, Kobe (JP); Masanori Kawano, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 0 days.

(21) Appl. No.: 14/838,014

(22) Filed: Aug. 27, 2015

(65) Prior Publication Data

US 2015/0369741 A1 Dec. 24, 2015

Related U.S. Application Data

(63) Continuation of application No. PCT/JP2014/055168, filed on Feb. 28, 2014.

(30) Foreign Application Priority Data

Feb. 28, 2013 (JP) .................................. 2013-039747

(51) Int. Cl.
| | |
|---|---|
| *G01N 21/64* | (2006.01) |
| *G01N 21/05* | (2006.01) |
| *G01N 33/50* | (2006.01) |
| *G01N 1/31* | (2006.01) |
| *G01N 33/493* | (2006.01) |
| *G01N 15/14* | (2006.01) |
| *G01N 15/00* | (2006.01) |
| *G01N 15/10* | (2006.01) |
| *G01N 21/53* | (2006.01) |

(52) U.S. Cl.
CPC ........... *G01N 21/6486* (2013.01); *G01N 1/31* (2013.01); *G01N 15/1459* (2013.01);
(Continued)

(58) Field of Classification Search
CPC ................. G01N 15/1459; G01N 1/31; G01N 2015/0069; G01N 2015/008;
(Continued)

(56) References Cited

U.S. PATENT DOCUMENTS 5,656,499 A * 8/1997 Chupp .................. B01F 5/0453
422/63
5,693,484 A * 12/1997 Nakamoto ............... C12Q 1/68
209/581
(Continued)

FOREIGN PATENT DOCUMENTS

| EP | 2 772 745 A1 | 9/2014 |
|---|---|---|
| JP | 08-170960 A | 7/1996 |

(Continued)

*Primary Examiner* — Maureen Wallenhorst
(74) *Attorney, Agent, or Firm* — Brinks Gilson & Lione

(57) ABSTRACT

A urine specimen analysis device includes a specimen drawing portion, a sample preparing portion, a measurement portion, and an information processing portion. The specimen drawing portion draws a first aliquot and a second aliquot from a urine specimen. The sample preparing portion prepares a first measurement sample by mixing the first aliquot and a first staining dye that stains red blood cells, and a second measurement sample by mixing the second aliquot and a second staining dye that stains nucleic acids. The measurement portion measures fluorescence emitted from the first measurement sample prepared by the sample preparing portion, and fluorescence emitted from the second measurement sample prepared by the sample preparing portion. The information processing portion detects at least red blood cells contained in the first measurement sample based on the fluorescence of the first measurement sample measured by the measurement portion, and at least white blood cells contained in the second measurement sample based on the fluorescence of the second measurement sample measured by the measurement portion.

20 Claims, 19 Drawing Sheets

(52) U.S. Cl.
CPC ........... *G01N 21/05* (2013.01); *G01N 33/493* (2013.01); *G01N 33/5094* (2013.01); *G01N 21/53* (2013.01); *G01N 21/645* (2013.01); *G01N 2015/008* (2013.01); *G01N 2015/0069* (2013.01); *G01N 2015/1006* (2013.01); *G01N 2201/0612* (2013.01)

(58) Field of Classification Search
CPC ........... G01N 2015/1006; G01N 21/05; G01N 21/53; G01N 21/645; G01N 21/6486; G01N 2201/0612; G01N 33/493; G01N 33/5094
USPC .............. 436/10, 63, 164, 172, 175; 422/73, 422/82.05, 82.08; 435/29, 372, 6.1, 288.7
See application file for complete search history.

(56) References Cited

U.S. PATENT DOCUMENTS

| | | | |
|---|---|---|---|
| 5,891,733 A | 4/1999 | Inoue | |
| 6,004,816 A | 12/1999 | Mizukami et al. | |
| 7,936,456 B2 * | 5/2011 | Narisada | G01N 15/12 356/336 |
| 2005/0202400 A1 | 9/2005 | Tsuji et al. | |
| 2007/0190525 A1 | 8/2007 | Gu et al. | |
| 2007/0269897 A1 | 11/2007 | Tanaka et al. | |
| 2009/0050821 A1 | 2/2009 | Tanaka et al. | |
| 2014/0242633 A1 * | 8/2014 | Fukuda | G01N 33/5094 435/39 |
| 2014/0356895 A1 * | 12/2014 | Tanaka | C12Q 1/02 435/29 |
| 2015/0247802 A1 * | 9/2015 | Ozasa | G01N 15/1429 435/6.15 |
| 2016/0061711 A1 * | 3/2016 | Deka | G01N 33/5094 435/7.24 |

FOREIGN PATENT DOCUMENTS

| | | |
|---|---|---|
| JP | 08-240520 A | 9/1996 |
| JP | 10-319010 A | 12/1998 |
| JP | 2007-309728 A | 11/2007 |
| JP | 2011-529186 A | 12/2011 |
| WO | WO 04/001408 A1 | 12/2003 |
| WO | WO 2007/076549 A2 | 7/2007 |

* cited by examiner

URINE SPECIMEN ANALYSIS DEVICE AND URINE SPECIMEN ANALYSIS METHOD

CROSS REFERENCE TO RELATED APPLICATIONS

This application is continuation of International Patent Application No. PCT/JP2014/055168, filed on Feb. 28, 2014, entitled "URINE SAMPLE ANALYSIS DEVICE AND URINE SAMPLE ANALYSIS METHOD", which claims priority to Japanese Patent Application No. 2013-039747, filed on Feb. 28, 2013, the entire contents of which are incorporated herein by reference.

FIELD OF THE INVENTION

The present invention relates to a urine specimen analysis device and a urine specimen analysis method for analyzing a urine specimen by measuring a measurement sample obtained by mixing the urine specimen and a reagent.

BACKGROUND

Specimen analysis that analyzes components contained in specimens, such as blood or urine, collected from living bodies is widely performed in the field of clinical tests, and, recently, specimen analysis devices that automatically perform specimen analysis are used.

US2009/050821A1 discloses an in-urine physical component analysis device for measuring physical components contained in urine. According to the in-urine physical component analysis device described in US2009/050821A1, a sucked urine specimen is divided into two aliquots, wherein a diluting solution and a first staining reagent that stains membranes are mixed with one of the aliquots to prepare a measurement sample for measuring relatively large in-urine physical components, such as red blood cells, white blood cells, epithelial cells, and casts, and this measurement sample is subjected to optical measurement, so that red blood cells, white blood cells, epithelial cells, casts, and the like are analyzed, whereas a diluting solution and a second staining reagent that stains nucleic acids are mixed with the other aliquot to prepare a measurement sample for measuring bacteria that are smaller than other in-urine physical components, and this measurement sample is subjected to optical measurement, so that bacteria are analyzed.

Analysis results of in-urine physical components are used to estimate which point in the kidneys and the urinary tract is abnormal, and analysis of in-urine physical components is widely performed as important screening tests. Accordingly, there is a demand for further improvement in the precision of analysis performed by in-urine physical component analysis devices.

SUMMARY OF THE INVENTION

The scope of the present invention is defined solely by the appended claims, and is not affected to any degree by the statements within this summary.

Solution to Problem

A first aspect of the present invention is directed to a urine specimen analysis device, including: a specimen drawing portion configured to draw a first aliquot and a second aliquot from a urine specimen; a sample preparing portion configured to prepare a first measurement sample by mixing the first aliquot and a first staining dye that stains red blood cells, and prepare a second measurement sample by mixing the second aliquot and a second staining dye that stains nucleic acids; a measurement portion configured to measure fluorescence emitted from the first measurement sample prepared by the sample preparing portion, and measure fluorescence emitted from the second measurement sample prepared by the sample preparing portion; and an information processing portion configured to detect at least red blood cells contained in the first measurement sample based on the fluorescence of the first measurement sample measured by the measurement portion, and detect at least white blood cells contained in the second measurement sample based on the fluorescence of the second measurement sample measured by the measurement portion.

A second aspect of the present invention is directed to a urine specimen analysis device, including: a sample preparing portion configured to prepare a measurement sample by mixing a urine specimen, a staining dye that stains nucleic acids of nucleated cells, and a hemolytic agent; a measurement portion configured to measure fluorescence emitted from the measurement sample prepared by the sample preparing portion, and obtain nucleic acid information relating to nucleic acids of nucleated cells contained in the measurement sample; and an information processing portion configured to classify the nucleated cells contained in the measurement sample into a plural types of cells based on the nucleic acid information obtained by the measurement portion.

A third aspect of the present invention is directed to a urine specimen analysis method, including: distributing a urine sample to a first aliquot and a second aliquot; preparing a first measurement sample by mixing the first aliquot and a first staining dye that stains red blood cells; measuring first fluorescence emitted from the prepared first measurement sample; detecting at least red blood cells contained in the first measurement sample based on the measured first fluorescence; preparing a second measurement sample by mixing the second aliquot and a second staining dye that stains nucleic acids; measuring second fluorescence emitted from the prepared second measurement sample; and detecting at least white blood cells contained in the second measurement sample based on the measured second fluorescence.

A fourth aspect of the present invention is directed to a urine specimen analysis method, including: preparing a measurement sample by mixing a urine specimen, a staining dye that stains nucleic acids of nucleated cells, and a hemolytic agent; measuring fluorescence emitted from the prepared measurement sample, thereby generating nucleic acid information relating to nucleic acids of nucleated cells contained in the measurement sample; and classifying the nucleated cells contained in the urine specimen into a plural types of cells based on the generated nucleic acid information.

DETAILED DESCRIPTION OF THE PREFERRED EMBODIMENTS

Hereinafter, a preferred embodiment of the present invention will be described with reference to the drawings.
Configuration of the Urine Specimen Analysis Device This embodiment will describe a urine specimen analysis device for analyzing in-urine physical components. The urine specimen analysis device according to this embodiment allows a urine specimen to be loaded into the device, and analyzes in-urine physical components (red blood cells, white blood cells, epithelial cells, casts, bacteria, etc.).

Figure 1:
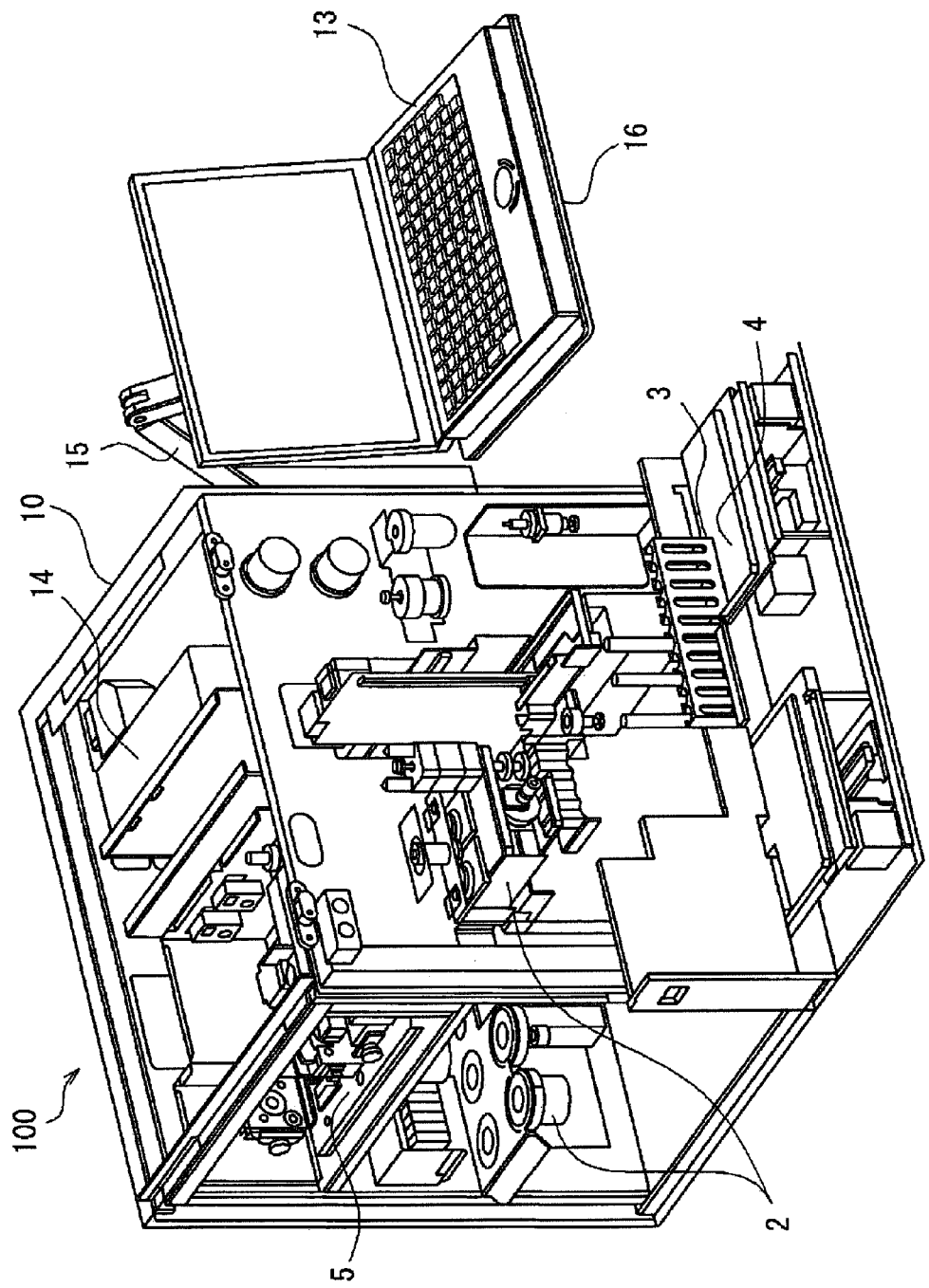
FIG. 1 is a perspective view showing the overall configuration of a urine specimen analysis device according to an embodiment.

FIG. 1 is an external perspective view showing the configuration of the urine specimen analysis device according to this embodiment. In FIG. 1, a urine specimen analysis device 100 includes a measurement unit 10 and an information processing portion 13. The measurement unit 10 includes a sample preparing portion 2 for preparing a measurement sample, a rack table 4 for transferring a sample rack (test tube rack) 3, an optical detection portion 5 for detecting information on physical components from the measurement sample, and a circuit portion 14. On a side face of the casing, a supporting stage 16 is arranged via an arm 15, and the information processing portion 13 is disposed on the supporting stage 16. The information processing portion 13 is data communicably connected to the circuit portion 14 of the measurement unit 10.

Figure 2:
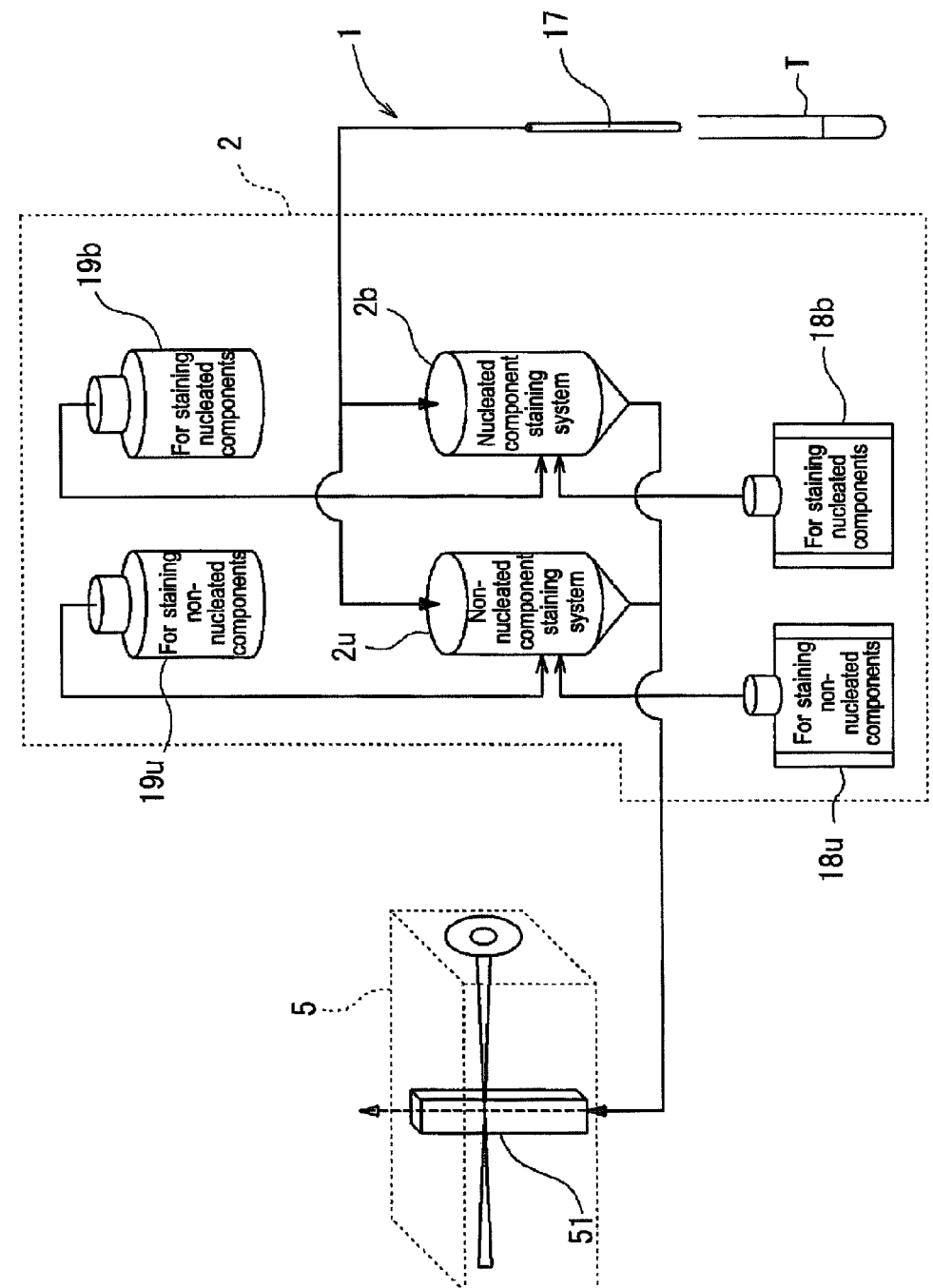
FIG. 2 is a diagram showing a schematic functional configuration of a sample preparing portion and an optical detection portion.

FIG. 2 is a diagram showing a schematic functional configuration of the sample preparing portion 2 and the optical detection portion 5. In the diagram, a urine specimen placed in a test tube T is sucked by an unshown syringe pump through a suction tube 17. The sucked urine specimen is dispensed by a specimen drawing portion 1 into the sample preparing portion 2. The sample preparing portion 2 in this embodiment includes a reaction tank 2*u* and a reaction tank 2*b*. The specimen drawing portion 1 takes out a predetermined amount of urine specimen and distributes an aliquot to each of the reaction tank 2*u* and the reaction tank 2*b*.

In the reaction tank 2*u*, the distributed aliquot is mixed with a diluting solution 19*u* and a staining solution 18*u*. Accordingly, physical components in the specimen are stained by a dye contained in the staining solution 18*u*. The mixture prepared in the reaction tank 2*u* is used to analyze particles not having nucleic acids, such as red blood cells, casts, crystals, mucus threads, or the like in urine. Hereinafter, the mixture prepared in the reaction tank 2*u* is referred to as a first measurement sample. Furthermore, particles basically not having nucleic acids, such as red blood cells, casts, crystals, mucus threads, and the like are referred to as non-nucleated components.

Meanwhile, in the reaction tank 2*b*, the distributed aliquot is mixed with a diluting solution 19*b* and a staining solution 18*b*. Accordingly, physical components in the specimen are stained by a dye contained in the staining solution 18*b*. The mixture prepared in the reaction tank 2*b* is used to analyze cells having nucleic acids, such as white blood cells, epithelial cells, fungi, sperm, *Trichomonas vaginalis*, bacteria, or the like in urine. Hereinafter, the mixture prepared in the reaction tank 2*b* is referred to as a second measurement sample. Furthermore, in-urine particles basically having nucleic acids, such as white blood cells, epithelial cells, fungi, sperm, *Trichomonas vaginalis*, bacteria, and the like are referred to as nucleated components. Strictly speaking, bacteria and sperm do not have a nucleus, but they are also regarded as belonging to nucleated components because nucleic acids are contained.

A tube extends from the reaction tanks 2*u* and 2*b* to a flow cell 51 of the optical detection portion 5, so that the measurement samples prepared in the reaction tanks 2*u* and 2*b* can be supplied to the flow cell 51. Of the two types of measurement samples prepared as described above, the first measurement sample in the reaction tank 2*u* is first sent to the optical detection portion 5, after which the second measurement sample in the reaction tank 2*b* is sent to the optical detection portion 5. Each of the first and second measurement samples sent to the optical detection portion 5 forms a thin flow enclosed in a sheath liquid in the flow cell 51, and the flow is irradiated with laser light. This operation is automatically performed by operating an unshown pump, solenoid valve, and the like under the control of a microcomputer 11 (control device), which will be described later.

As the staining solution 18u for staining non-nucleated components, a fluorescent dye that is more easily bonded to lipids and proteins of cell membranes than to nucleic acids is selected. Such a dye is preferably a dye that does not affect the forms of red blood cells, among cyanine-based, styryl-based, and acridine-based dyes. The dye that stains non-nucleated physical components is preferably a lipid-soluble carbocyanine dye, particularly preferably an indocarbocyanine dye, an oxacarbocyanine dye, or the like. Specific examples of the indocarbocyanine dye include DiI (1,1'-dioctadecyl-3,3,3',3'-tetramethylindocarbocyanine perchlorate), DiD (1,1'-dioctadecyl-3,3,3',3'-tetramethylindodicarbocyanine), DiR (1,1'-dioctadecyltetramethyl indotricarbocyanine iodide), and the like. Examples of the oxacarbocyanine dye include DiOC2(3) (3,3'-diethyloxacarbocyanine iodide), DiOC3(3) (3,3-dipropyloxacarbocyanine iodide), DiOC4(3) (3,3'-dibutyloxacarbocyanine iodide), DiOC5(3) (3,3-dipentyloxacarbocyanine iodide), and the like. The dye that stains non-nucleated components used in this embodiment is particularly preferably DiOC3(3) (3,3-dipropyloxacarbocyanine iodide).

The diluting solution 19u is a reagent that consists primarily of buffer. The diluting solution 19u contains an osmotic pressure compensating agent in order to obtain stable fluorescence signals without hemolyzing red blood cells. The osmotic pressure of the diluting solution 19u is adjusted to 100 to 600 mOsm/kg so as to be suitable for classification and measurement. When the urine specimen, the staining solution 18u, and the diluting solution 19u are mixed, cell membranes or proteins of non-nucleated components are stained.

As the staining solution 18b for staining nucleated components, a fluorescent dye that is more easily bonded to nucleic acids than to lipids and proteins is selected. More specifically, the staining solution 18b contains an intercalator or a dye that can be bonded to minor grooves for specifically staining nucleic acids. Examples of the intercalator include known dyes such as cyanine-based, acridine-based, and phenanthridium-based dyes. Examples of the cyanine-based intercalator include SYBR Green I and Thiazole orange. Examples of the acridine-based intercalator include Acridinorange. Examples of the phenanthridium-based intercalator include propidium iodide and ethidium bromide. Examples of the dye that can be bonded to minor grooves include known dyes such as DAPI and Hoechst. Examples of the Hoechst dye that can be bonded to minor grooves include Hoechst 33342 and Hoechst 33258. In this embodiment, the staining solution 18b preferably contains a cyanine-based intercalator, particularly preferably SYBR GreenI or Thiazole orange.

The diluting solution 19b contains a cationic surfactant for facilitating membrane penetration of the staining solution 18b by damaging cell membranes, and for hemolyzing red blood cells and making impurities such as red blood cell fragments smaller. The diluting solution 19b may contain a nonionic surfactant instead of the cationic surfactant. When the urine specimen, the staining solution 18b, and the diluting solution 19b are mixed, in-urine physical components having nucleic acids are stained to levels corresponding to their configurations and characteristics.

As described above, the diluting solution 19b contains a surfactant having a hemolytic action. Accordingly, red blood cells contained in a urine specimen can be hemolyzed, and non-nucleated components can be precisely measured even in a urine specimen containing a large amount of red blood cells. Furthermore, in measurement of nucleated components, a reagent having a hemolytic action is used, so that cell membranes can be damaged, and nucleic acids can be efficiently stained. This aspect also contributes to improvement in the precision of measurement of nucleated components.

The urine specimen analysis device 100 of this embodiment prepares, from one urine specimen, a first measurement sample for measuring non-nucleated components in urine and a second measurement sample for measuring nucleated components in urine. The urine specimen analysis device 100 measures non-nucleated components such as red blood cells using the first measurement sample, and measures nucleated cells such as white blood cells using the second measurement sample. The first measurement sample contains a fluorescent dye that easily stains lipids or proteins of cell membranes. The second measurement sample contains a fluorescent dye that easily stains nucleic acids. Thus, according to this embodiment, in-urine particles can be precisely classified or identified using differences in the characteristics of cells, that is, the stain levels according to the nucleic acid amount and the membrane stainability, without the influence of changes in the cell forms. Although in-urine particles may be damaged when passing through a glomerulus or may be deformed due to a change in the osmotic pressure when passing through a ureter, according to this embodiment, precise analysis can be performed using differences in the stainability, without the influence of changes in the particle forms.

In this embodiment, one optical detection portion 5 is used for both measurement of the first measurement sample and measurement of the second measurement sample. Accordingly, the device configuration can be simplified, and the device can be made smaller.

Figure 3:
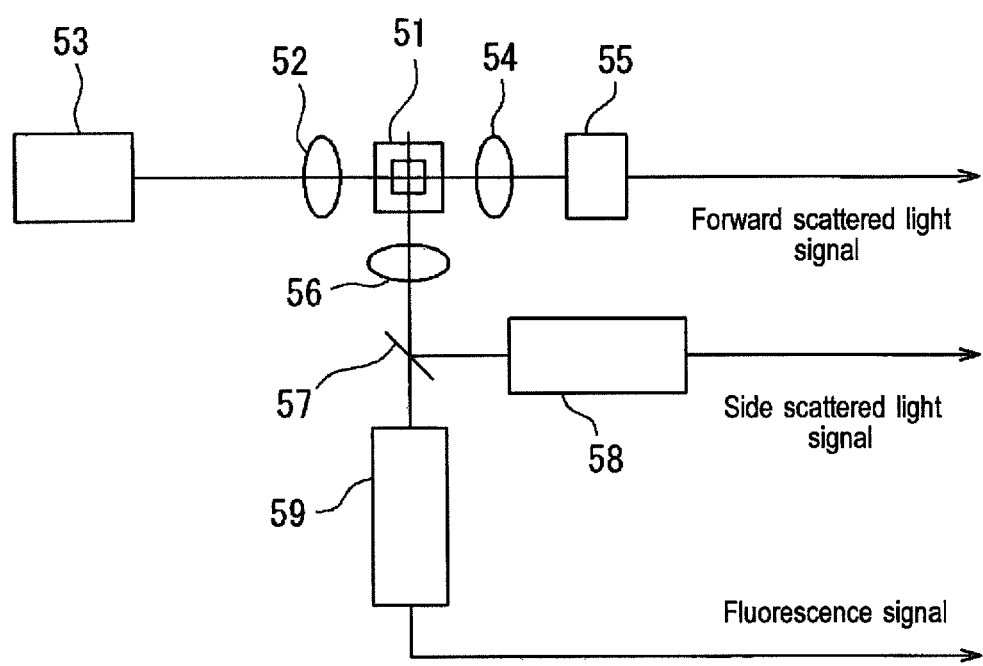
FIG. 3 is a diagram showing the configuration of the optical detection portion.

FIG. 3 is a diagram showing the configuration of the optical detection portion 5. A condenser lens 52 converges laser light emitted from a semiconductor laser light source 53, on the flow cell 51. A converging lens 54 converges forward scattered light emitted from physical components in a measurement sample, on a first scattered light receiving portion 55 configured by a photodiode. Another converging lens 56 converges side scattered light and fluorescence emitted from the physical components, on a dichroic mirror 57. The dichroic mirror 57 reflects the side scattered light to a second scattered light receiving portion 58 configured by a photomultiplier tube, and allows the fluorescence to pass therethrough toward a fluorescence receiving portion 59 configured by a photomultiplier tube. The first scattered light receiving portion 55, the second scattered light receiving portion 58, and the fluorescence receiving portion 59 convert optical signals into electrical signals, and respectively output a forward scattered light signal (hereinafter, referred to as "FSC"), a side scattered light signal (hereinafter, referred to as "SSC"), and a fluorescence signal (hereinafter, referred to as "FL"). The first scattered light receiving portion 55, the fluorescence receiving portion 59, and the second scattered light receiving portion 58 can switch the amplification factor at the time of photoelectric conversion, that is, the light sensitivity between a low sensitivity and a high sensitivity by switching the drive voltage. The light sensitivity is switched by a microcomputer 11, which will be described later.

Note that, as the light source, a gas laser light source also can be used instead of the semiconductor laser light source, but the semiconductor laser light source is preferably used because the cost is lower, the size is smaller, and the power consumption is lower.

Figure 4:
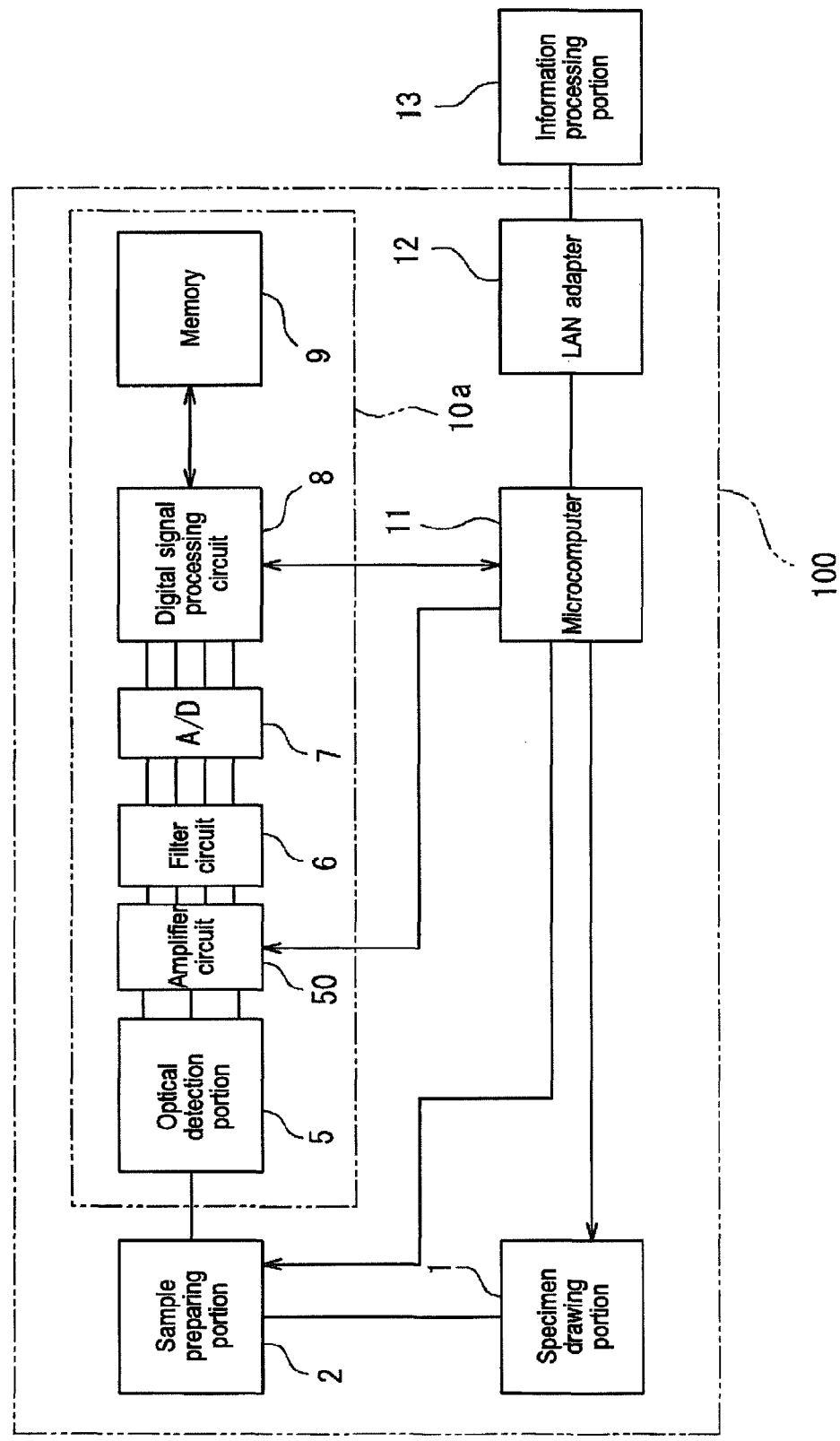
FIG. 4 is a block diagram showing the configuration of the urine specimen analysis device according to the embodiment.

FIG. 4 is a block diagram showing the configuration of the urine specimen analysis device 100. In the diagram, the measurement unit 10 includes the specimen drawing portion 1, the sample preparing portion 2, and the optical detection portion 5 described above, as well as an amplifier circuit 50 that amplifies an output signal of the optical detection portion 5, a filter circuit 6 that performs filtering processing on an output signal from the amplifier circuit 50, an A/D converter 7 that converts an output signal (analog signal) of the filter circuit 6 into a digital signal, a digital signal processing circuit 8 that performs predetermined waveform processing on the digital signal, a memory 9 that is connected to the digital signal processing circuit 8, the microcomputer 11 that is connected to the sample preparing portion 2, the amplifier circuit 50, and the digital signal processing circuit 8, and a LAN adapter 12 that is connected to the microcomputer 11. The information processing portion 13 is connected via the LAN adapter 12 to the measurement unit 10 through a LAN cable. The information processing portion 13 analyzes measurement data obtained by the measurement unit 10. The optical detection portion 5, the amplifier circuit 50, the filter circuit 6, the A/D converter 7, the digital signal processing circuit 8, and the memory 9 form a measurement portion 10a that measures a measurement sample, thereby generating measurement data.

The optical detection portion 5 amplifies each of the FSC, SSC, and FL signals using a preamplifier. Each amplified signal is input via a signal channel to the amplifier circuit 50. An FSC signal channel is connected to a main amplifier (FSC amplifier) for amplifying FSC. An SSC signal channel is connected to a main amplifier (SSC amplifier) for amplifying SSC. An FL signal channel is branched into two channels between the preamplifier and the amplifier circuit 50. One of the signal channels is connected to a main amplifier with a high amplification factor of the amplifier circuit 50. The other signal channel is connected to a main amplifier with a low amplification factor. Accordingly, FLH amplified at a high amplification factor and FLL amplified at a low amplification factor are obtained from FL corresponding to one particle. Hereinafter, the main amplifier with a high amplification factor is referred to as an FLH amplifier and FL input to the FLH amplifier is referred to as "FLH". Also, the main amplifier with a low amplification factor is referred to as an FLL amplifier, and FL input to the FLL amplifier is referred to as "FLL".

The amplifier circuit 50 amplifies four types of signals consisting of FSC, SSC, FLH, and FLL, according to a set gain. The amplifier circuit 50 can set a plurality of different gains. The microcomputer 11 can individually adjust the gain of each preamplifier of the amplifier circuit 50 in a stepwise manner. The gain can be set among three levels consisting of low level, middle level, and high level. The high level has the highest gain, and the low level has the lowest gain.

Figure 5:
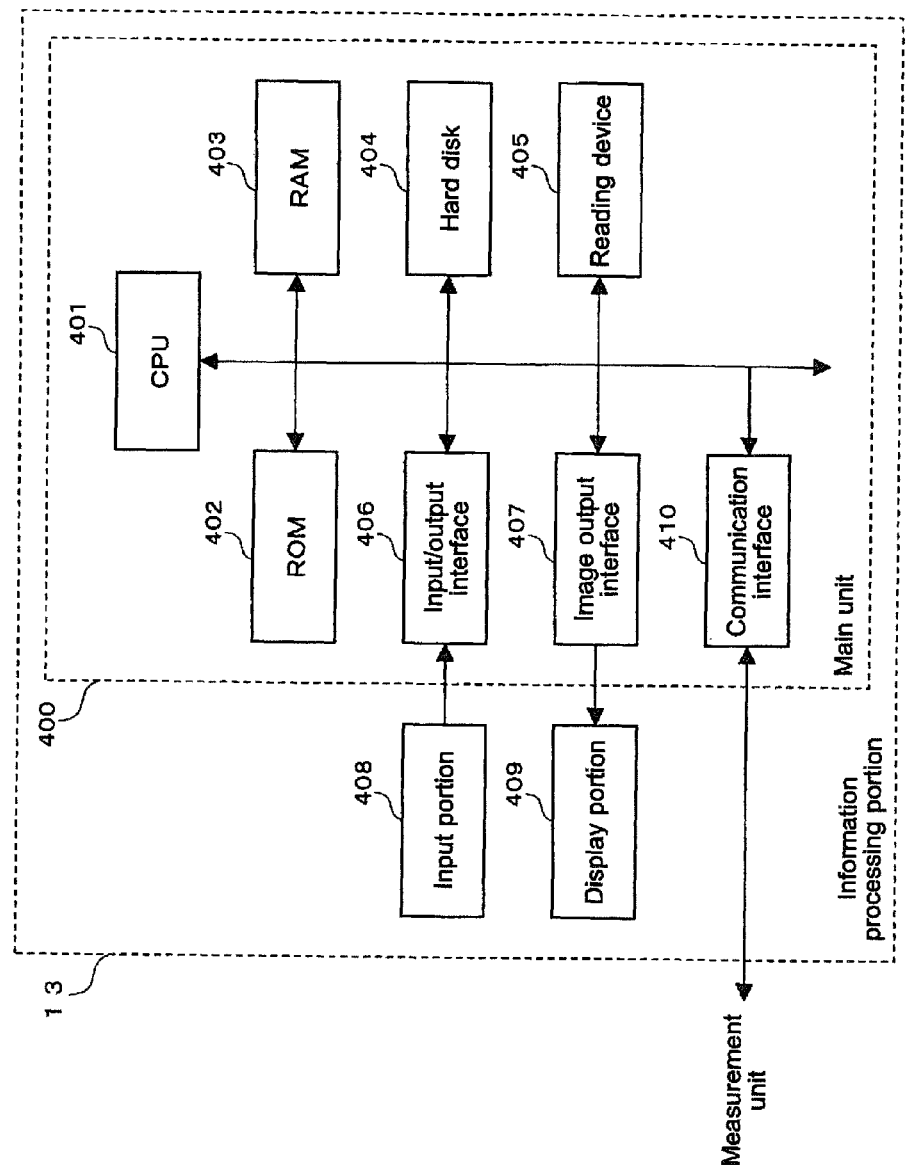
FIG. 5 is a block diagram showing the configuration of an information processing portion.

FIG. 5 is a block diagram showing the configuration of the information processing portion 13. The information processing portion 13 is configured by a personal computer, including a main unit 400, an input portion 408, and a display portion 409. The main unit 400 has a CPU 401, a ROM 402, a RAM 403, a hard disk 404, a reading device 405, an input/output interface 406, an image output interface 407, and a communication interface 410.

The CPU 401 executes a computer program stored in the ROM 402 and a computer program loaded into the RAM 403. The RAM 403 is used to read a computer program stored in the ROM 402 and the hard disk 404. The RAM 403 is used also as a working area of the CPU 401 during execution of these computer programs.

In the hard disk 404, various computer programs that are to be executed by the CPU 401 and data that can be used to execute the computer programs, such as operating systems and application programs, are installed. That is to say, in the hard disk 404, computer programs for analyzing measurement data given from the measurement unit 10 and outputting analysis results are installed.

The reading device 405 is configured by a CD drive, a DVD drive, or the like, and can read computer programs and data stored in a storage medium. The input/output interface 406 is connected to the input portion 408 including a mouse and a keyboard, and, when a user uses the input portion 408, data is input to the information processing portion 13. The image output interface 407 is connected to the display portion 409 configured by a liquid crystal panel or the like, and outputs video signals according to image data to the display portion 409. The display portion 409 displays an image based on the input video signals. Furthermore, the information processing portion 13 is connected via the communication interface 410 to the measurement unit 10, and can exchange data with the measurement unit 10 via the communication interface 410.

Operation of the Urine Specimen Analysis Device

Hereinafter, an operation of the urine specimen analysis device according to this embodiment will be described.

Figure 6:
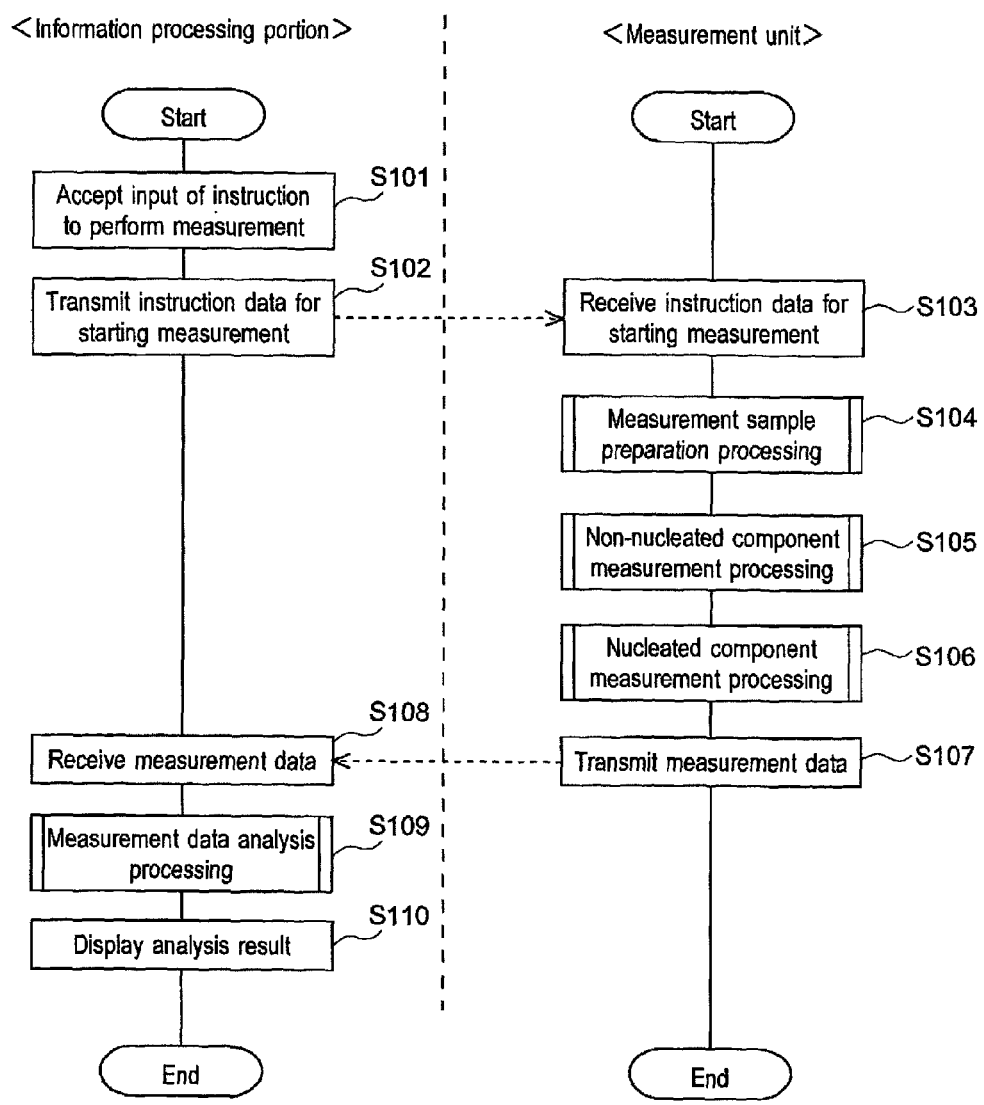
FIG. 6 is a flowchart showing a procedure of specimen measurement processing of the urine specimen analysis device according to the embodiment.

FIG. 6 is a flowchart showing a procedure of specimen measurement processing of the urine specimen analysis device 100. First, an instruction to perform measurement is input by a user via the input portion 408 of the information processing portion 13 (Step S101). Upon receiving this instruction, the CPU 401 transmits instruction data for giving the measurement unit 10 an instruction to start measurement (Step S102). If the measurement unit 10 receives the instruction data (Step S103), the microcomputer 11 performs measurement sample preparation processing (Step S104), non-nucleated component measurement processing (Step S105), and nucleated component measurement processing (Step S106).

Figure 7:
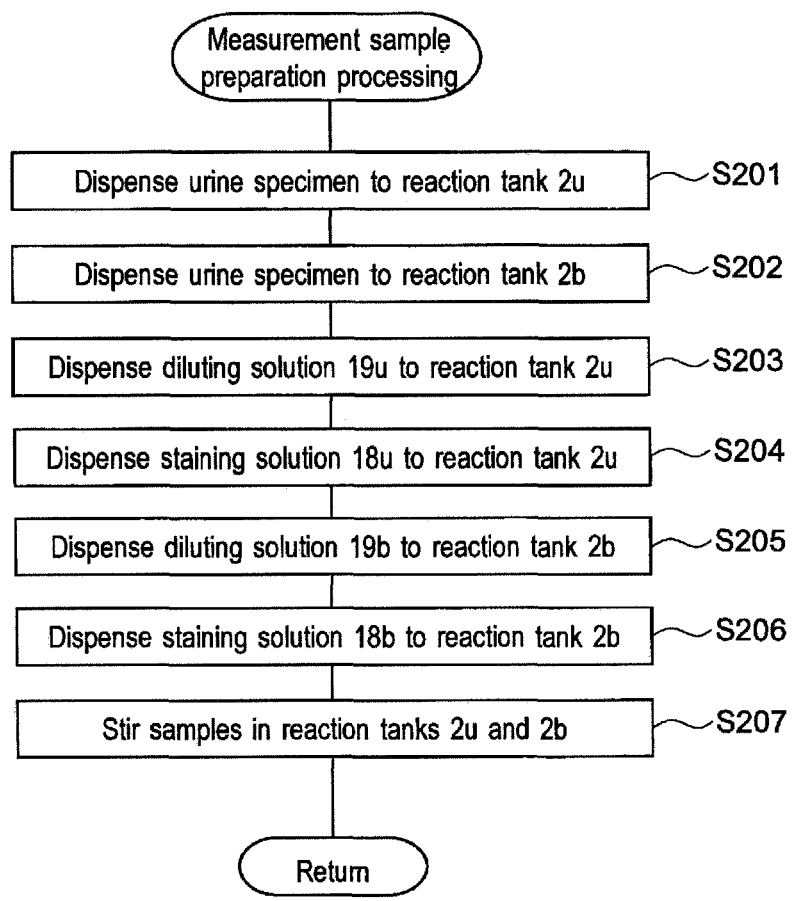
FIG. 7 is a flowchart showing a procedure of measurement sample preparation processing.

FIG. 7 is a flowchart showing a procedure of the measurement sample preparation processing. In the measurement sample preparation processing, first, the microcomputer 11 controls the specimen drawing portion 1 so that a predetermined amount of urine specimen is sucked from the test tube T into the suction tube 17. The microcomputer 11 controls the specimen drawing portion 1 so that a predetermined amount of urine specimen aliquot is dispensed to each of the reaction tank 2u and the reaction tank 2b (Steps S201 and S202).

The microcomputer 11 controls the sample preparing portion 2 so that the following steps S203 to S207 are performed. In steps S203 and S204, a predetermined amount of diluting solution 19u and staining solution 18u are taken out and dispensed into the reaction tank 2u (Steps S203 and S204). In steps S205 and S206, a predetermined amount of diluting solution 19b and staining solution 18b are taken out and dispensed into the reaction tank 2b (Steps S205 and S206). Each of the reaction tank 2u and the reaction tank 2b is heated by an unshown heater to a predetermined temperature, and, in this state, the mixture in each tank is stirred by a propeller-like stirrer (not shown) (Step S207). Accordingly, a first measurement sample for measuring non-nucleated components is prepared in the reaction tank 2u, and a second measurement sample for measuring nucleated components is prepared in the reaction tank 2*b*. If the process in step S207 ends, the microcomputer 11 returns the procedure to the main routine.

Figure 8:
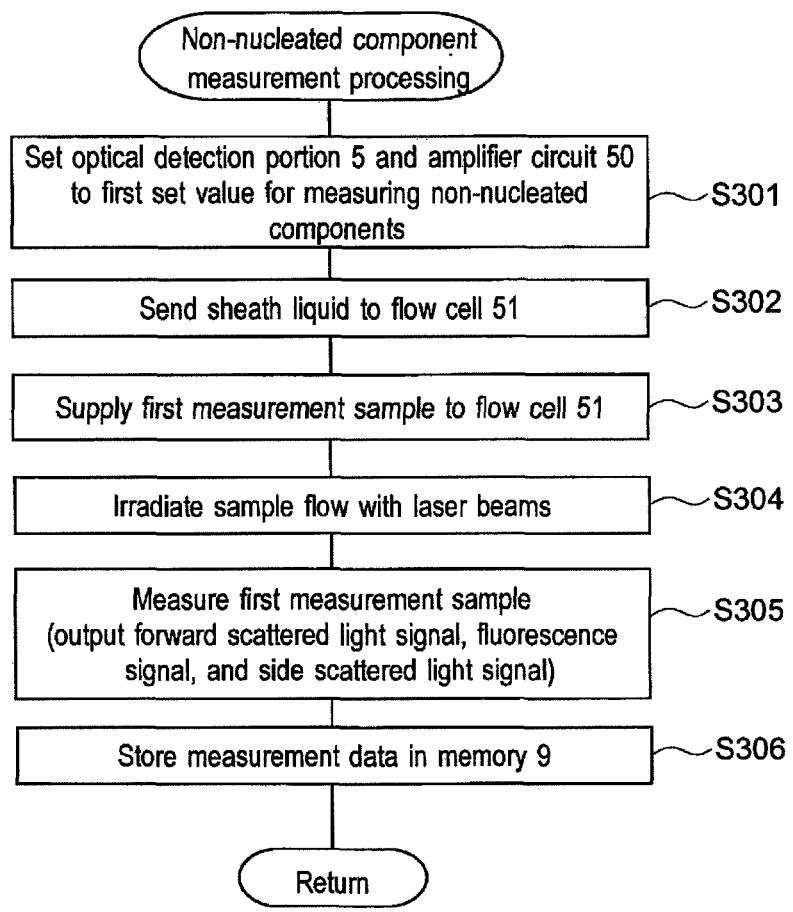
FIG. 8 is a flowchart showing a procedure of non-nucleated component measurement processing.

FIG. 8 is a flowchart showing a procedure of non-nucleated component measurement processing. In the non-nucleated component measurement processing, first, the microcomputer 11 sets the light sensitivity of the optical detection portion 5 and the gain of the amplifier circuit 50 to a first set value for measuring non-nucleated components (Step S301).

Each of the first set value and a second and a third set value, which will be described later, contains a value of the light sensitivity of each light receiving portion of the optical detection portion 5 and a value of the gain of the amplifier circuit 50. Hereinafter, the values are distinguished from each other by referring to the former as "light sensitivity" and the latter as "gain". The amplification factor of a signal is determined by the product of these values. Hereinafter, a value determined by the product of the light sensitivity and the gain is referred to as an "amplification factor".

If the first set value is set, the light sensitivity of the optical detection portion 5 is set to the low sensitivity. Furthermore, the gain of the FSC amplifier is set to the middle level. The FLL amplifier is set to the middle level. The FLH amplifier is set to the low level. The FLH amplification factor determined by the first set value is lower than an FLH2 amplification factor determined by the third set value, which will be described later.

The microcomputer 11 sends a sheath liquid to the flow cell 51 by driving an unshown compressor (Step S302). In a state where the sheath liquid is continuously supplied to the flow cell 51, the microcomputer 11 supplies the first measurement sample from the reaction tank 2*u* to the flow cell 51 (Step S303).

Accordingly, the sheath liquid and the first measurement sample are simultaneously supplied to the flow cell 51, and a flow of the first measurement sample enclosed in the sheath liquid is formed in the flow cell 51. The thus formed sample flow is irradiated with a laser beam from the light source 53 (Step S304), and a beam spot is formed on the flow cell 51. When particles pass through the beam spot on the flow cell 51, the particles are irradiated with light from the light source 53, and forward scattered light, fluorescence, and side scattered light are generated from the particles. The forward scattered light, the fluorescence, and the side scattered light are respectively received by the first scattered light receiving portion 55, the fluorescence receiving portion 59, and the second scattered light receiving portion 58, and are converted into electrical signals (Step S305). Accordingly, each time particles pass through the flow cell 51, output signals of the first scattered light receiving portion 55, the second scattered light receiving portion 58, and the fluorescence receiving portion 59 change in a pulsed manner.

The electrical signals corresponding to the light receiving levels of the first scattered light receiving portion 55 and the second scattered light receiving portion 58 are output as FSC and SSC. The electrical signals corresponding to the light receiving levels of the fluorescence receiving portion 59 are output as two signals consisting of FLH and FLL. At that time, FSC, SSC, FLH, and FLL are output at the light sensitivity (low sensitivity) determined by the first set value set in step S301. The output signals are amplified by the main amplifier of the amplifier circuit 50 at the gain determined by the first set value.

Accordingly, four types of optical signals consisting of a low-sensitivity fluorescence signal (hereinafter, referred to as FLL), a high-sensitivity fluorescence signal (hereinafter, referred to as FLH), FSC, and SSC are obtained from each particle of the first measurement sample.

The FSC, FLL, FLH, and SSC amplified by the amplifier circuit 50 set to the first set value are subjected to filtering processing by the filter circuit 6. These signals are converted by the A/D converter 7 into digital signals, and are subjected to predetermined signal processing by the digital signal processing circuit 8.

The digital signal processing circuit 8 performs signal processing, thereby extracting parameters used in analysis processing, from the optical signals (FSC, SSC, FLL, and FLH). The analysis parameters include a forward scattered light intensity (hereinafter, referred to as "FSCP"), a pulse width of the forward scattered light (hereinafter, referred to as "FSCW"), a side scattered light intensity (hereinafter, referred to as "SSCP"), a low-sensitivity fluorescence intensity (hereinafter, referred to as "FLLP"), a pulse width of the low-sensitivity fluorescence signal (hereinafter, referred to as "FLLW"), a pulse area of the low-sensitivity fluorescence signal (hereinafter, referred to as "FLLA"), a high-sensitivity fluorescence intensity (hereinafter, referred to as "FLHP"), a pulse width of the high-sensitivity fluorescence signal (hereinafter, referred to as "FLHW"), and a pulse area of the high-sensitivity fluorescence signal (hereinafter, referred to as "FLHA").

Figure 9A:
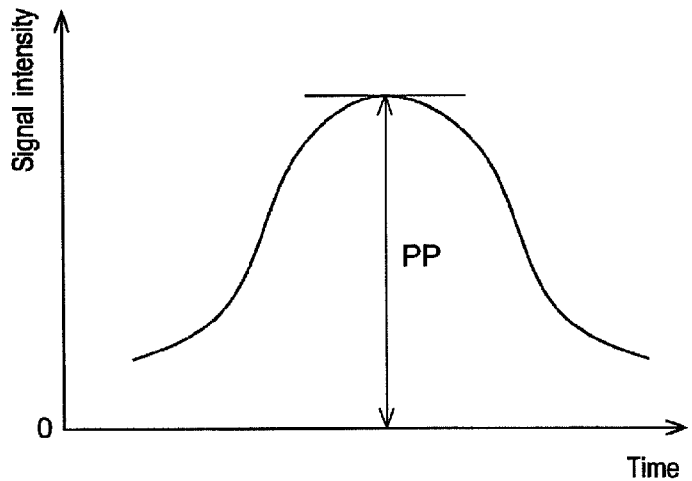
FIG. 9A is a schematic graph illustrating an intensity of an optical signal.
Figure 9B:
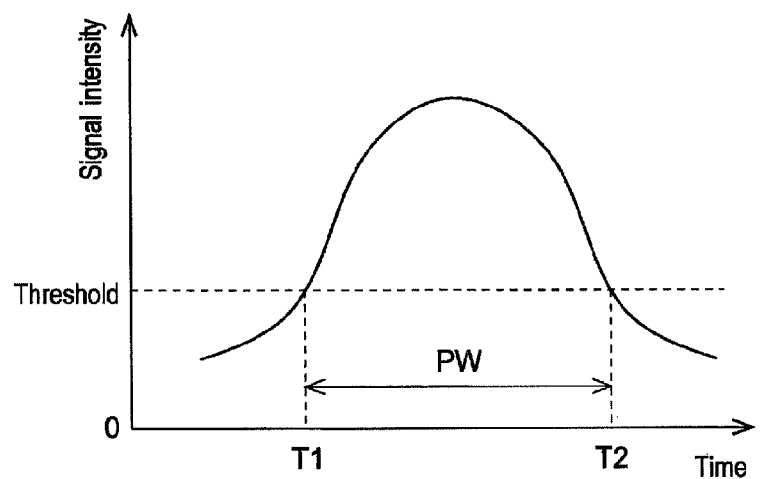
FIG. 9B is a schematic graph illustrating a pulse width of an optical signal.
Figure 9C:
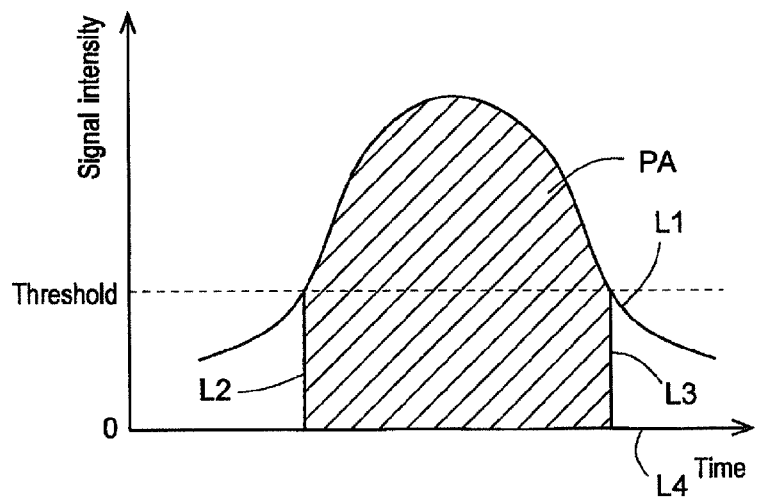
FIG. 9C is a schematic graph illustrating a pulse area of an optical signal.

Hereinafter, extraction of analysis parameters will be described with reference to FIGS. 9A to 9C. There are three types of analysis parameters consisting of "intensity", "pulse width", and "pulse area" for each optical signal. The intensity is represented by P. The pulse width is represented by W. The pulse area is represented by A. As described above, each time particles pass through the flow cell 51, electrical signals output from the light receiving portions change in a pulsed manner according to the characteristics of the particles. Each of the intensities of the optical signals such as FSCP, SSCP, FLLP, and FLHP is obtained as a pulse peak height P as shown in FIG. 9A. Each of the pulse widths of the optical signals such as FSCW, FLLW, and FLHW is obtained as an interval W from a time T1 when a pulse exceeds a predetermined threshold to a time T2 when the pulse drops below the threshold as shown in FIG. 9B. Each of the pulse areas of the optical signals such as FLLA and FLHA is obtained as an area of a region PA (region indicated by diagonal lines in the diagram) defined by a signal pulse waveform line L1, straight lines L2 and L3 indicating the times when the optical signal intensity is at a predetermined threshold, on both sides of the pulse, and a straight line L4 at which the optical signal intensity is 0, as shown in FIG. 9C, that is, as the time integral value of the signal intensity.

Note that the above-described method for extracting analysis parameters is merely an example, and other extraction methods may be used. The pulse area may be an approximate as long as it is a value reflecting the area under the pulse time curve, and is not limited to the time integral value. For example, the pulse area may be the product of the pulse width and the peak height, or may be the triangle area obtained from the pulse width and the peak height. Furthermore, when extracting the time integral value, the base may not be a straight line at which the intensity is 0, and may be set as appropriate. For example, the base may be at the predetermined threshold shown in FIG. 9C, or may be at a reference value that can be determined at the pulse value obtained when only the sheath liquid flows through the flow cell 51.

Reference is again made to FIG. 8. The parameters extracted from the optical signals as described above are stored as measurement data in the memory 9 (Step S306). When the above-described procedure ends, the microcomputer 11 returns the procedure to the main routine.

Figure 10:
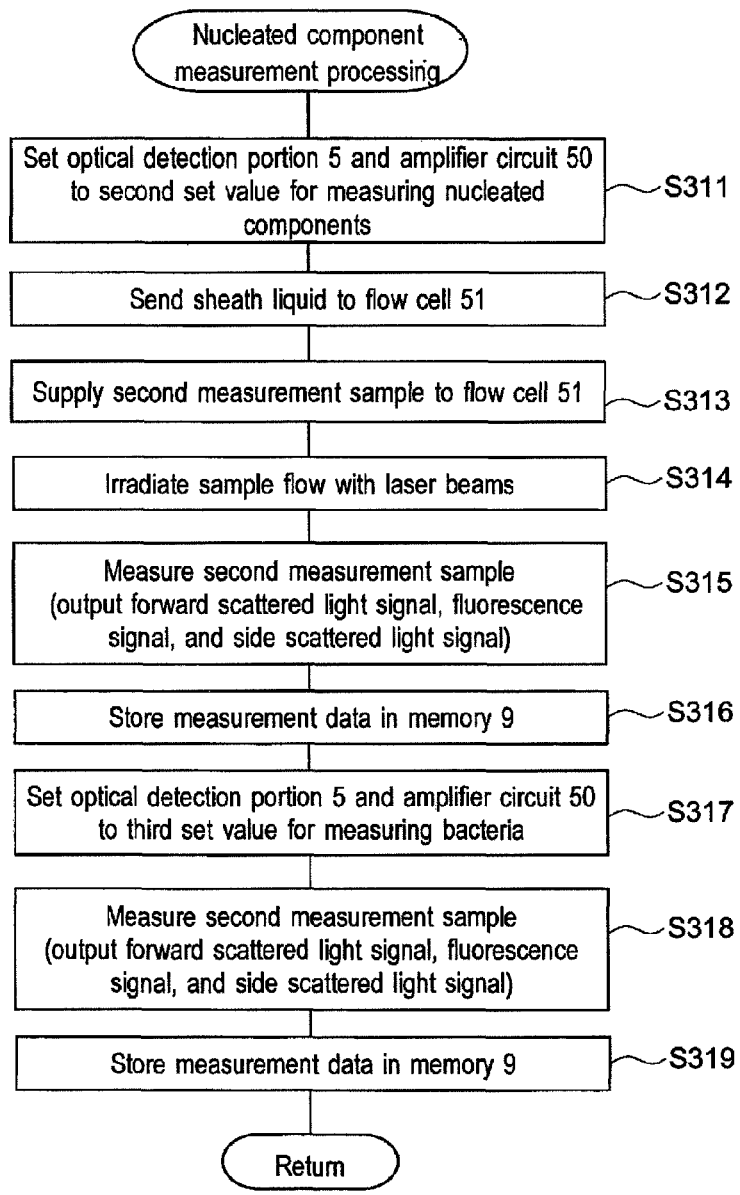
FIG. 10 is a flowchart showing a procedure of nucleated component measurement processing.

FIG. 10 is a flowchart showing a procedure of nucleated component measurement processing. In the nucleated component measurement processing, first, the microcomputer 11 sets the light sensitivity of the optical detection portion 5 and the gain of the amplifier circuit 50 to a second set value (Step S311). The second set value is a set value for measuring nucleated components such as white blood cells, epithelial cells, and fungi.

If the second set value is set, the light sensitivity of the optical detection portion 5 is set to the low sensitivity. Furthermore, the FSC amplifier is set to the low level. The FLL amplifier is set to the low level. The FLH amplifier is set to the middle level. The FLH amplification factor determined by the second set value is lower than an FLH2 amplification factor determined by the third set value, which will be described later.

Next, the microcomputer 11 sends a sheath liquid to the flow cell 51 by driving an unshown compressor (Step S312). In a state where the sheath liquid is continuously supplied to the flow cell 51, the microcomputer 11 supplies the second measurement sample from the reaction tank 2b to the flow cell 51 (Step S313).

Accordingly, the sheath liquid and the second measurement sample are simultaneously supplied to the flow cell 51, and a flow of the second measurement sample enclosed in the sheath liquid is formed in the flow cell 51. The thus formed sample flow is irradiated with a laser beam from the light source 53 (Step S314). Accordingly, forward scattered light, fluorescence, and side scattered light are generated from the nucleated cells. The forward scattered light, the fluorescence, and the side scattered light are respectively received by the first scattered light receiving portion 55, the fluorescence receiving portion 59, and the second scattered light receiving portion 58, and are converted into electrical signals (Step S315).

The optical detection portion 5 outputs FSC, FLH, FLL, and SSC at the light sensitivity determined by the second set value. The output signals are amplified by the amplifier circuit 50 at the gain determined by the second set value.

Accordingly, four types of optical signals consisting of a low-sensitivity fluorescence signal FLL, a first high-sensitivity fluorescence signal (hereinafter, referred to as "FLH1"), FSC, and SSC are obtained from each particle of the second measurement sample.

The amplified signals are subjected to filtering processing by the filter circuit 6. These signals are converted by the A/D converter 7 into digital signals, and are subjected to predetermined signal processing by the digital signal processing circuit 8. With this signal processing, an FSC peak value is extracted as FSCP. An FSC pulse width is extracted as FSCW. An SSC peak value is extracted as SSCP. An FLL peak value is extracted as FLLP. An FLL pulse width is extracted as FLLW. An FLL pulse area is extracted as FLLA. An FLH1 peak value is extracted as a first high-sensitivity fluorescence intensity (hereinafter, referred to as "FLHP1"). An FLH1 pulse width is extracted as a first high-sensitivity fluorescence pulse width (hereinafter, referred to as "FLHW1"). An FLH1 pulse area is extracted as a first high-sensitivity fluorescence pulse area (hereinafter, referred to as "FLHA1"). Data of the extracted parameters is stored as measurement data in the memory 9 (Step S316).

When a predetermined period of time has passed after the supply of the second measurement sample to the flow cell 51 is started, the microcomputer 11 changes the light sensitivity of the optical detection portion 5 and the gain of the amplifier circuit 50 to a third set value (Step S317). The third set value is a set value for measuring bacteria.

If the third set value is set, the light sensitivity of the optical detection portion 5 is set to the high sensitivity. Furthermore, the FSC amplifier is set to the high level. The FLH amplifier is set to the high level. The FLL amplifier is not used.

The light sensitivity (high sensitivity) of the fluorescence receiving portion 59 at the third set value is five times the light sensitivity (low sensitivity) of the fluorescence receiving portion 59 at the second set value. The reason for this is that a bacterium has a size smaller than that of any other nucleated cell, and therefore has a fluorescence amount smaller than that in measurement of any other nucleated cell. When the light sensitivity of the fluorescence receiving portion 59 at the third set value is set to be higher than the light sensitivity at the second set value, the light sensitivity becomes suitable for bacteria, and a trace amount of fluorescence emitted from bacteria can be precisely detected. Furthermore, when the gain of the FSC amplifier at the third set value is set to the high level, very small bacteria can be precisely detected.

In a state where the optical detection portion 5 and the amplifier circuit 50 is set to the third set value, the second measurement sample is measured (Step S318). Accordingly, the optical detection portion 5 outputs signals at the light sensitivity determined by the third set value, and the output signals are amplified by the amplifier circuit 50 at the gain determined by the third set value. The FLH output from the optical detection portion 5 when the third set value is set is amplified by the FLH amplifier of the amplifier circuit 50 and is obtained as a second high-sensitivity fluorescence signal (hereinafter, referred to as "FLH2").

Accordingly, two types of optical signals consisting of a second high-sensitivity fluorescence signal FLH2 and FSC are obtained from each particle of the second measurement sample.

The FSC and FLH2 amplified by the amplifier circuit 50 are subjected to filtering processing by the filter circuit 6, and are then converted by the A/D converter 7 into digital signals and subjected to predetermined signal processing by the digital signal processing circuit 8. With this signal processing, an FSC peak is extracted as FSCP. An FSC pulse width is extracted as FSCW. An SSC peak value is extracted as SSCP. FLH2 peak value is extracted as a second high-sensitivity fluorescence intensity (hereinafter, referred to as "FLHP2"). An FLH2 pulse width is extracted as a second high-sensitivity fluorescence pulse width (hereinafter, referred to as "FLHW2"). An FLH2 pulse area is extracted as a second high-sensitivity fluorescence pulse area (hereinafter, referred to as "FLHA2"). Data of the extracted parameters is stored as measurement data in the memory 9 (Step S319). When the above-described procedure ends, the microcomputer 11 returns the procedure to the main routine.

After the nucleated component measurement processing, the microcomputer 11 transmits the measurement data generated by the non-nucleated component measurement processing and the nucleated component measurement processing, to the information processing portion 13 (Step S107), and ends the procedure.

Figure 11:
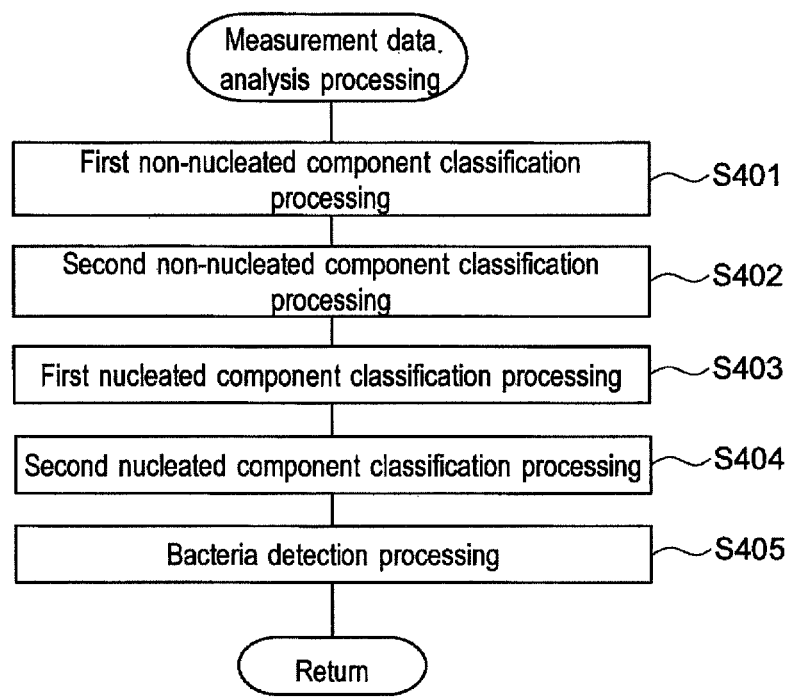
FIG. 11 is a flowchart showing a procedure of measurement data analysis processing.

If the information processing portion 13 receives the measurement data (Step S108), the CPU 401 performs measurement data analysis processing (Step S109), thereby generating a urine specimen analysis result, and stores the analysis result in the hard disk 404. FIG. 11 is a flowchart showing a procedure of measurement data analysis processing. The measurement data analysis processing includes first non-nucleated component classification processing (Step S401), second non-nucleated component classification processing (Step S402), first nucleated component classification processing (Step S403), second nucleated component classification processing (Step S404), and bacteria detection processing (Step S405).

Figure 12:
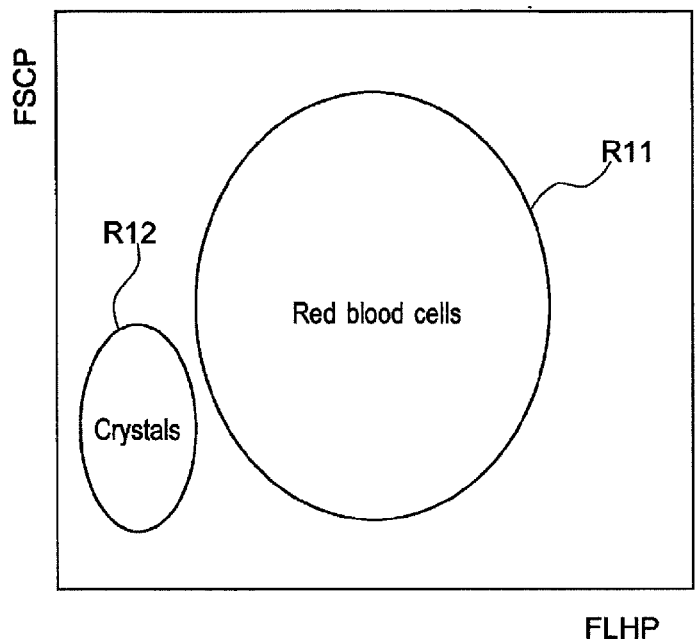
FIG. 12 is a diagram showing distributions of red blood cells and crystals in a fluorescence intensity-forward scattered light intensity region.

In the first non-nucleated component classification processing S401, red blood cells and crystals are detected using the FSC and FLH obtained by measuring the first measurement sample, and the numbers thereof are counted. Red blood cells and crystals are detected using FLH, because each of them is less stainable than any of a cast, a mucus thread, and the like, and therefore has a smaller fluorescence amount. FIG. 12 is a diagram showing distributions of red blood cells and crystals in FLHP-FSCP space. In FIG. 12, the horizontal axis indicates FLHP, and the vertical axis indicates FSCP. As shown in the diagram, a difference is seen in FLHP between a red blood cell distribution region R11 and a crystal distribution region R12. The reason for this is that there is a difference in the dye stainability between a crystal and a red blood cell. Accordingly, red blood cells and crystals are classified based on FLHP. In the first non-nucleated component classification processing, particles contained in the region R11 shown in the diagram are detected as red blood cells, and the number thereof is counted. Furthermore, particles contained in the region R12 shown in the diagram are detected as crystals, and the number thereof is counted.

Figure 13A:
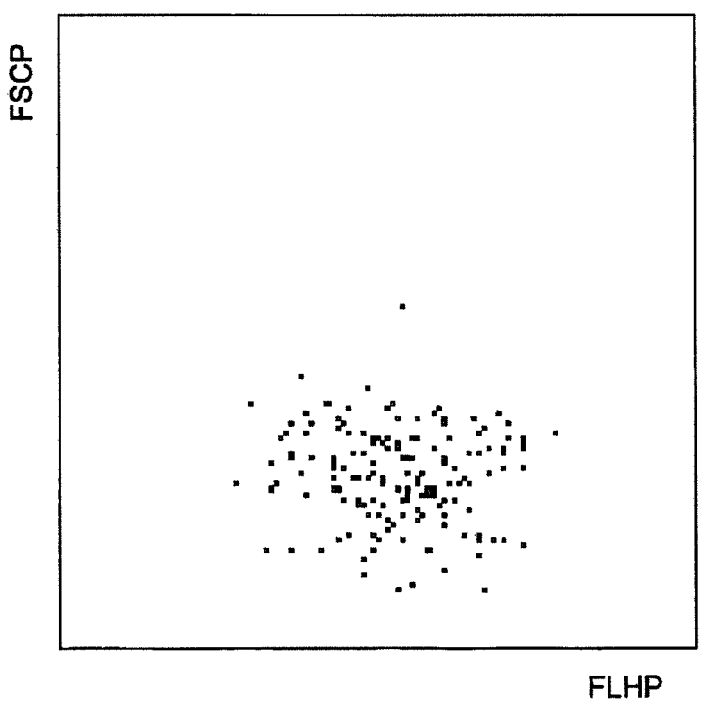
FIG. 13A is a scattergram showing an exemplary detection result of red blood cells.
Figure 13B:
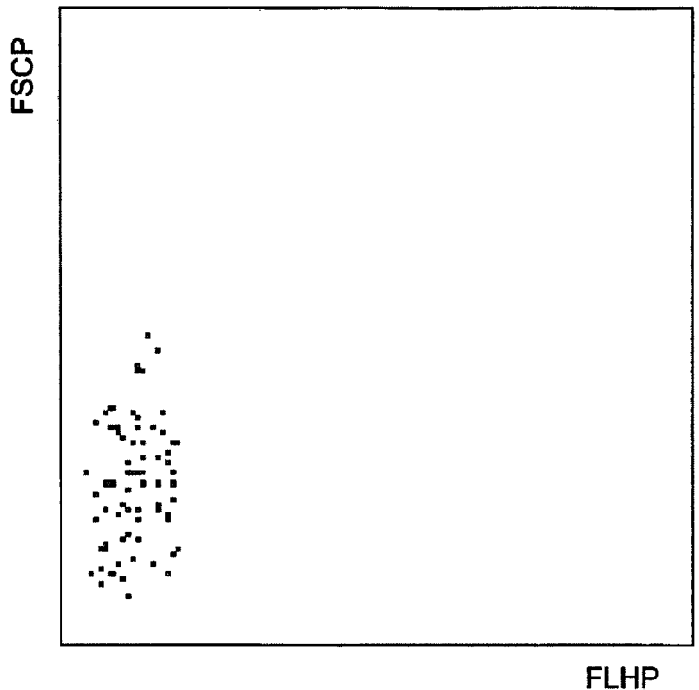
FIG. 13B is a scattergram showing an exemplary detection result of crystals.

FIGS. 13A and 13B show specific detection results in the first non-nucleated component classification processing S401. FIG. 13A is a scattergram showing an exemplary detection result of red blood cells, and FIG. 13B is a scattergram showing an exemplary detection result of crystals. FIG. 13A shows a result obtained by measuring a specimen containing red blood cells, and FIG. 13B shows a result obtained by measuring a specimen containing crystals.

Figure 14:
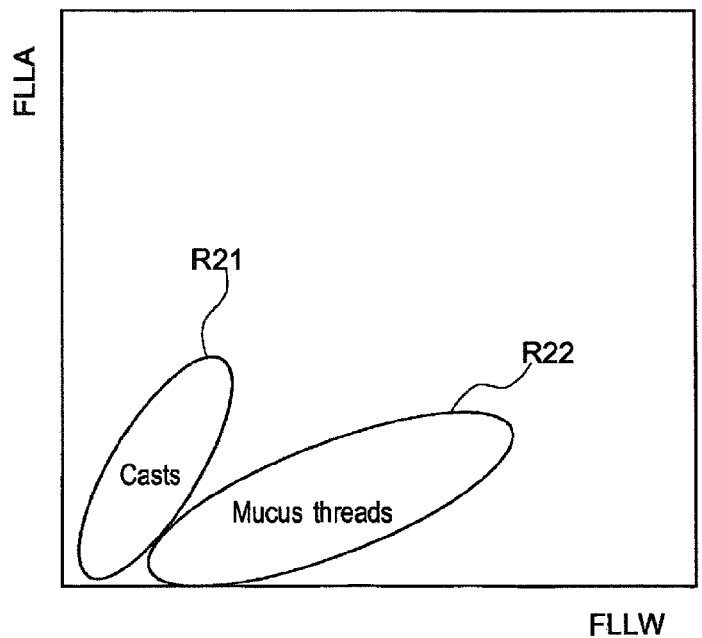
FIG. 14 is a diagram showing distributions of casts and mucus threads in a fluorescence pulse width-fluorescence pulse area region.

In the second non-nucleated component classification processing S402, casts and mucus threads are detected using the FLL obtained by measuring the first measurement sample, and the numbers thereof are counted. Casts and mucus threads are detected using FLL, because each of them is more stainable than any of a red blood cell and a crystal, and therefore has a larger fluorescence amount. FIG. 14 is a diagram showing distributions of casts and mucus threads in FLLW-FLLA space. In the diagram, the horizontal axis indicates FLLW, and the vertical axis indicates FLLA. As shown in the diagram, in the FLLW-FLLA region, casts and mucus threads appear in different regions R21 and R22. The reason for this is that there is a difference in the stainability and the thickness of stained substrate, between a cast and a mucus thread. Accordingly, casts and mucus threads are classified based on FLLW and FLLA. In the second non-nucleated component classification processing, particles contained in the region R21 shown in the diagram are detected as casts, and the number thereof is counted. Furthermore, particles contained in the region R22 shown in the diagram are detected as mucus threads, and the number thereof is counted.

Figure 15A:
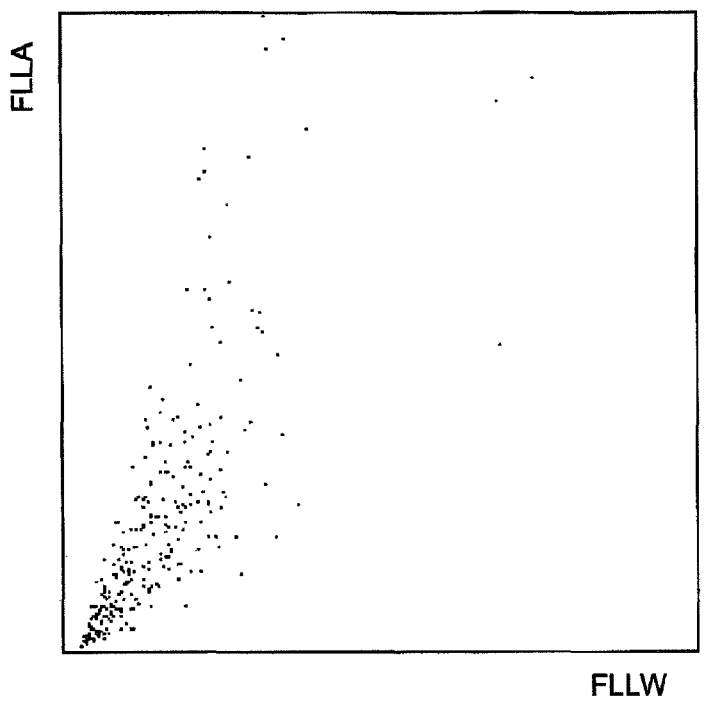
FIG. 15A is a scattergram showing an exemplary detection result of casts.
Figure 15B:
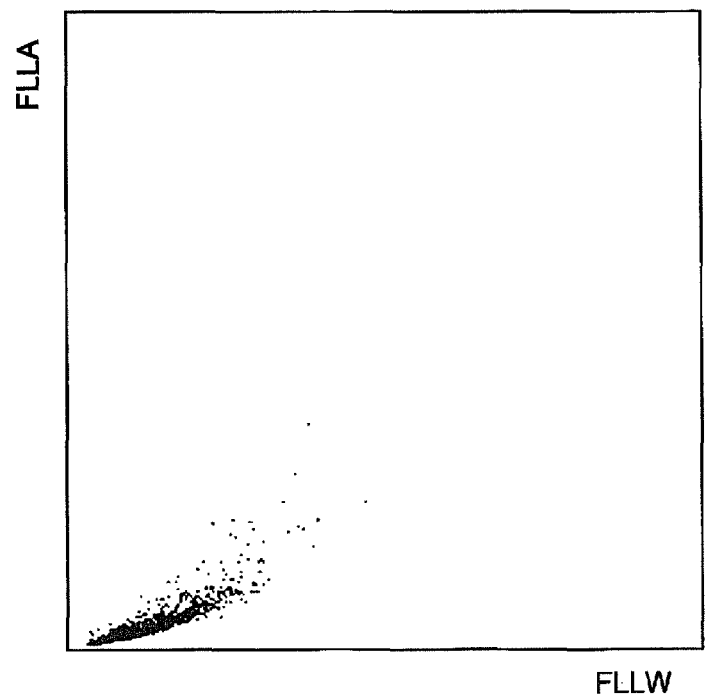
FIG. 15B is a scattergram showing an exemplary detection result of mucus threads.

FIGS. 15A and 15B show specific detection results in the second non-nucleated component classification processing S402. FIG. 15A is a scattergram showing an exemplary detection result of casts, and FIG. 15B is a scattergram showing an exemplary detection result of mucus threads. FIG. 15A shows a result obtained by measuring a specimen containing casts, and FIG. 15B shows a result obtained by measuring a specimen containing mucus threads.

Next, in-urine cells having nucleic acids are classified by the first nucleated component classification processing, the second nucleated component classification processing, and the bacteria detection processing.

Figure 16:
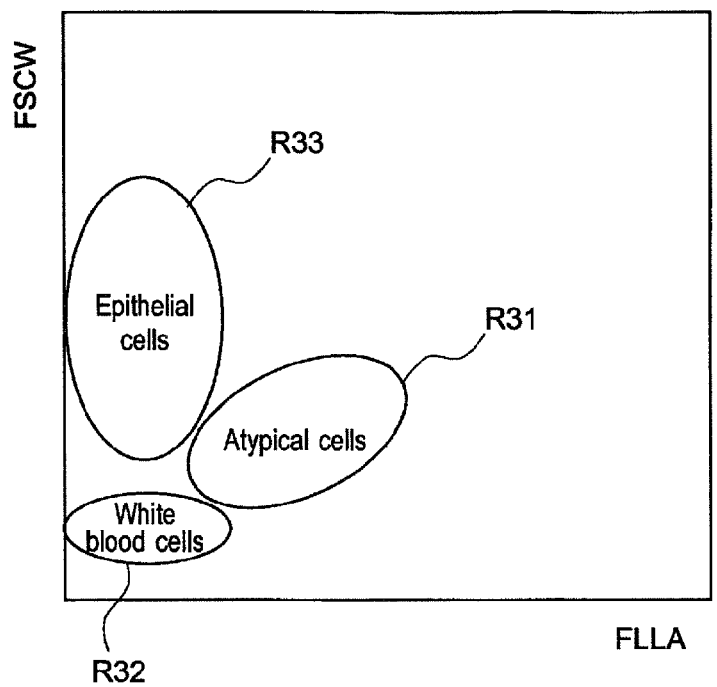
FIG. 16 is a diagram showing distributions of white blood cells, atypical cells, and epithelial cells in a fluorescence pulse area-forward scattered light pulse width region.

In the first nucleated component classification processing S403, atypical cells, white blood cells, and epithelial cells are detected using the FSC and FLL obtained by measuring the second measurement sample, and the numbers thereof are counted. Atypical cells, white blood cells, and epithelial cells are detected using FLL, because each of them has a nucleic acid amount larger than that of any of a sperm, *Trichomonas vaginalis*, a fungus, and the like, and therefore has a larger fluorescence amount. FIG. 16 is a diagram showing distributions of white blood cells, atypical cells, and epithelial cells in FLLA-FSCW space. In the diagram, the horizontal axis indicates FLLA, and the vertical axis indicates FSCW. As shown in the diagram, a difference is seen in FLLA between white blood cells and epithelial cells, and atypical cells. The reason for this is that there is substantially no difference in the nucleic acid amount between a white blood cell and an epithelial cell, and an atypical cell has a nucleic acid amount larger than that of any of a white blood cell and an epithelial cell. Furthermore, a difference is seen in FSCW between white blood cells and epithelial cells. The reason for this is that an epithelial cell has a size larger than that of a white blood cell. Accordingly, white blood cells, epithelial cells, and atypical cells are classified based on FLLA and FSCW. In the first nucleated component classification processing, particles contained in a region R31 shown in the diagram are detected as atypical cells, and the number thereof is counted. Furthermore, particles contained in a region R32 shown in the diagram are detected as white blood cells, and the number thereof is counted. Furthermore, particles contained in a region R33 shown in the diagram are detected as epithelial cells, and the number thereof is counted.

Figure 17A:
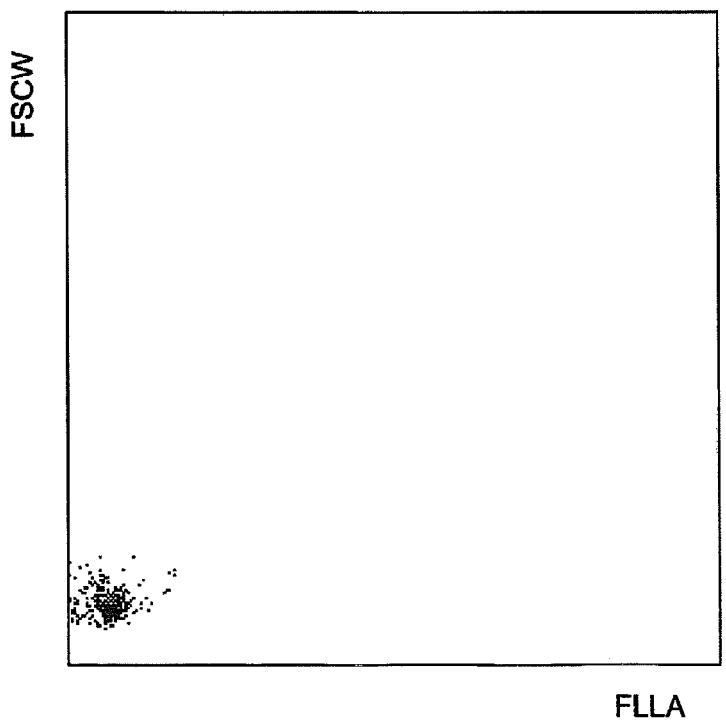
FIG. 17A is a scattergram showing an exemplary detection result of white blood cells.
Figure 17B:
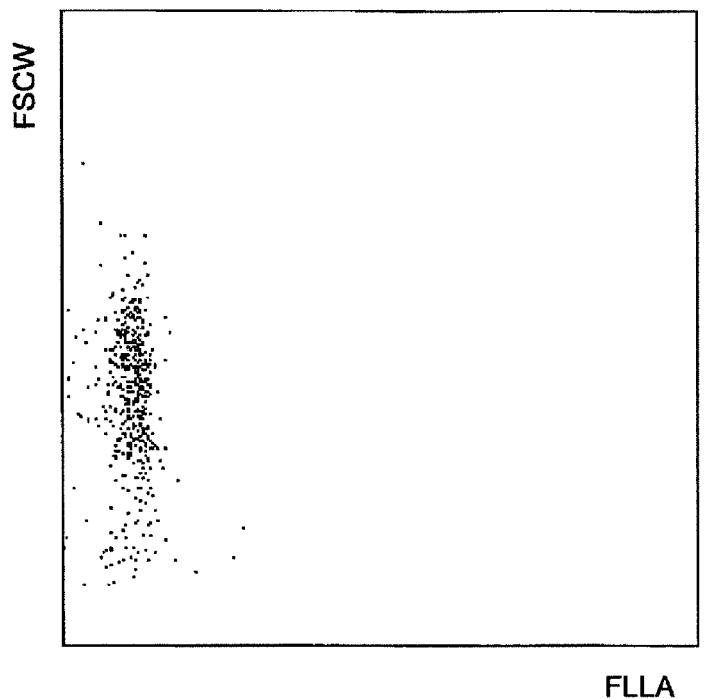
FIG. 17B is a scattergram showing an exemplary detection result of epithelial cells.
Figure 17C:
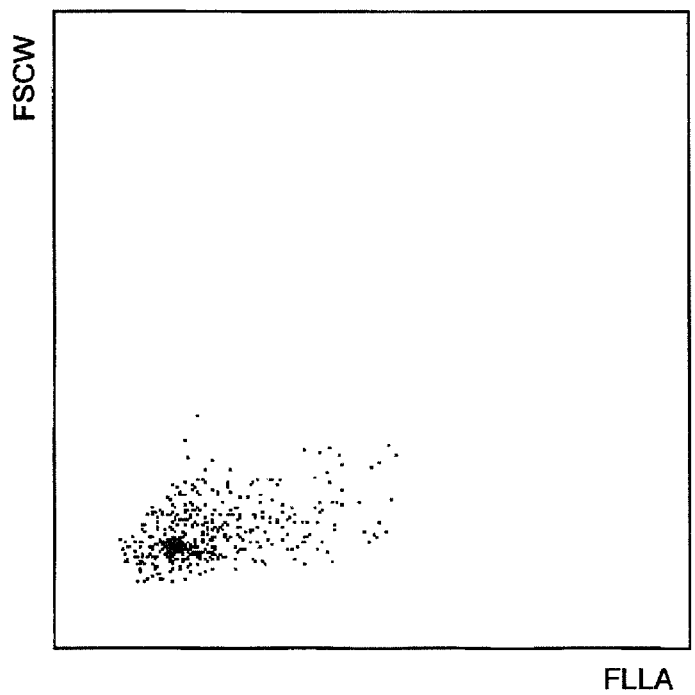
FIG. 17C is a scattergram showing an exemplary detection result of atypical cells.

FIGS. 17A to 17C show specific detection results in the first nucleated component classification processing S403. FIG. 17A is a scattergram showing an exemplary detection result of white blood cells, FIG. 17B is a scattergram showing an exemplary detection result of epithelial cells, and FIG. 17C is a scattergram showing an exemplary detection result of atypical cells. FIG. 17A shows a result obtained by measuring a specimen containing white blood cells, FIG. 17B shows a result obtained by measuring a specimen containing epithelial cells, and FIG. 17C shows a result obtained by measuring a specimen containing atypical cells.

Figure 18:
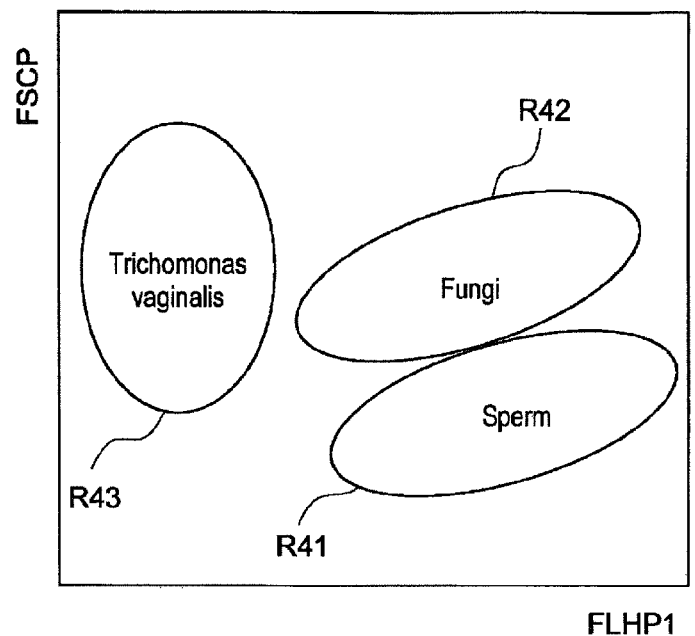
FIG. 18 is a diagram showing distributions of sperm, *Trichomonas vaginalis*, and fungi in a fluorescence intensity-forward scattered light intensity region.

In the second nucleated component classification processing S404, sperm, *Trichomonas vaginalis*, and fungi are detected using the FSC and FLH1 obtained by measuring the second measurement sample, and the numbers thereof are counted. FIG. 18 is a diagram showing distributions of sperm, *Trichomonas vaginalis*, and fungi in FLHP1-FSCP space. Sperm, *Trichomonas vaginalis*, and fungi are detected using FLH1, because each of them has a nucleic acid amount smaller than that of any of a white blood cell, an epithelial cell, and an atypical cell, and therefore has a smaller fluorescence amount. In the diagram, the horizontal axis indicates FLHP1, and the vertical axis indicates FSCP. As shown in the diagram, distribution regions of sperm, fungi, and *Trichomonas vaginalis* in FLHP1-FSCP space are different. The reason for this is that there is a difference in the nucleic acid amount and in the size between a sperm, a fungus, and *Trichomonas vaginalis*. Accordingly, sperm, *Trichomonas vaginalis*, and fungi are classified based on FLHP1 and FSCP. In the second nucleated component classification processing, particles contained in a region R41 shown in the diagram are detected as sperm, and the number thereof is counted. Furthermore, particles contained in a region R42 shown in the diagram are detected as fungi, and the number thereof is counted. Furthermore, particles contained in a region R43 shown in the diagram are detected as *Trichomonas vaginalis*, and the number thereof is counted.

Figure 19A:
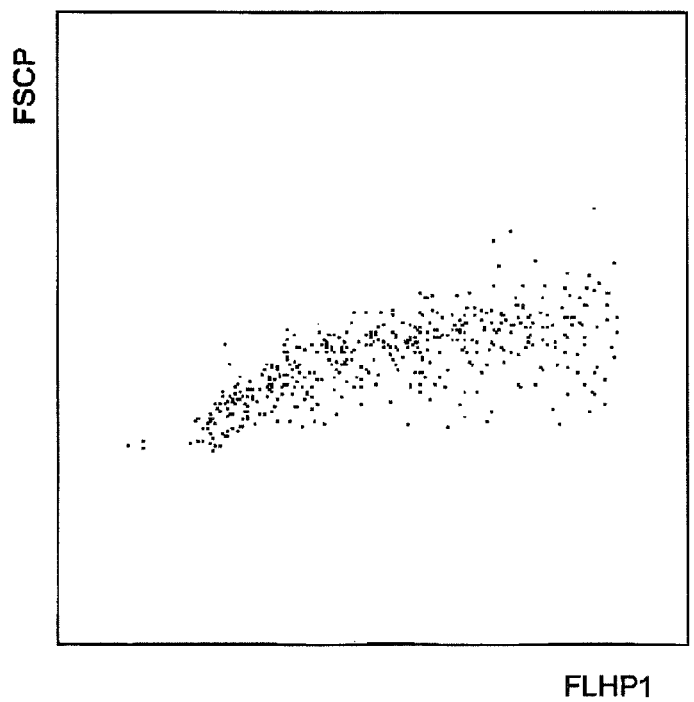
FIG. 19A is a scattergram showing an exemplary detection result of fungi.
Figure 19B:
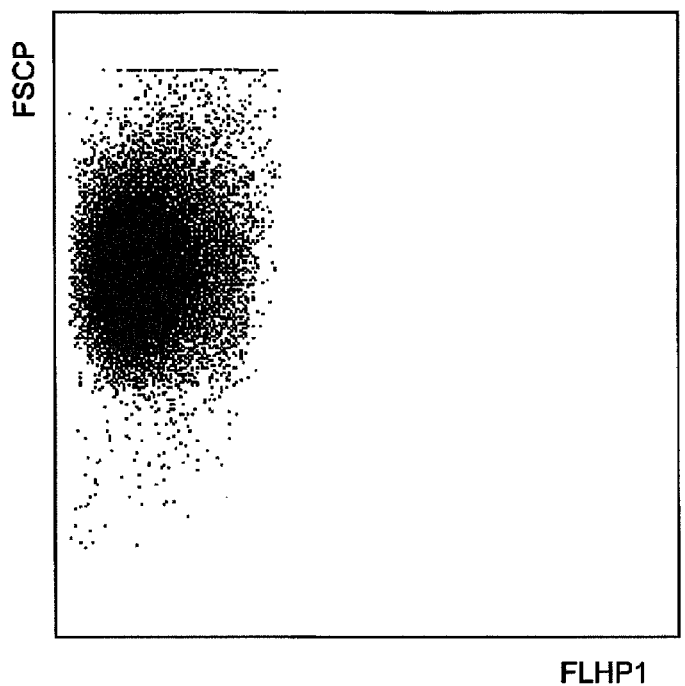
FIG. 19B is a scattergram showing an exemplary detection result of *Trichomonas vaginalis*.
Figure 19C:
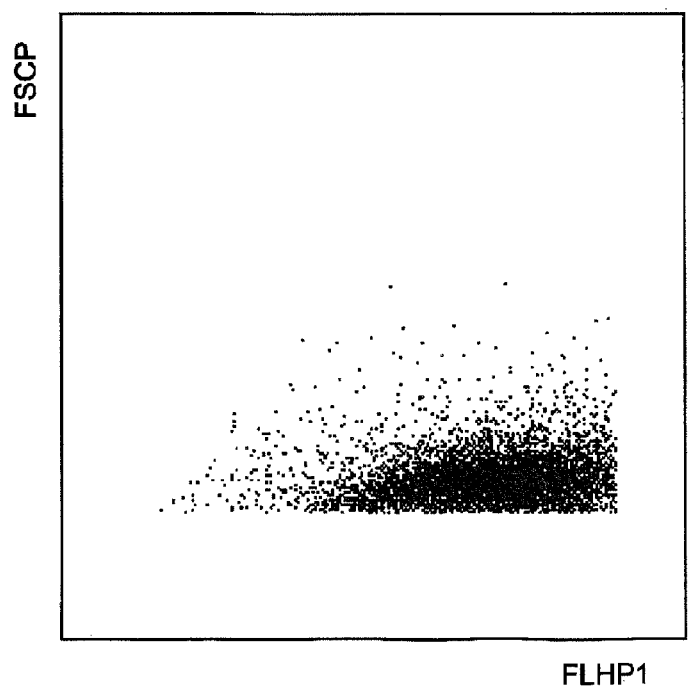
FIG. 19C is a scattergram showing an exemplary detection result of sperm.

FIGS. 19A to 19C show specific detection results in the second nucleated component classification processing S404. FIG. 19A is a scattergram showing an exemplary detection result of fungi, FIG. 19B is a scattergram showing an exemplary detection result of *Trichomonas vaginalis*, and FIG. 19C is a scattergram showing an exemplary detection result of sperm. FIG. 19A shows a result obtained by measuring a specimen containing fungi, FIG. 19B shows a result obtained by measuring a specimen containing *Trichomonas vaginalis*, and FIG. 19C shows a result obtained by measuring a specimen containing sperm.

Figure 20:
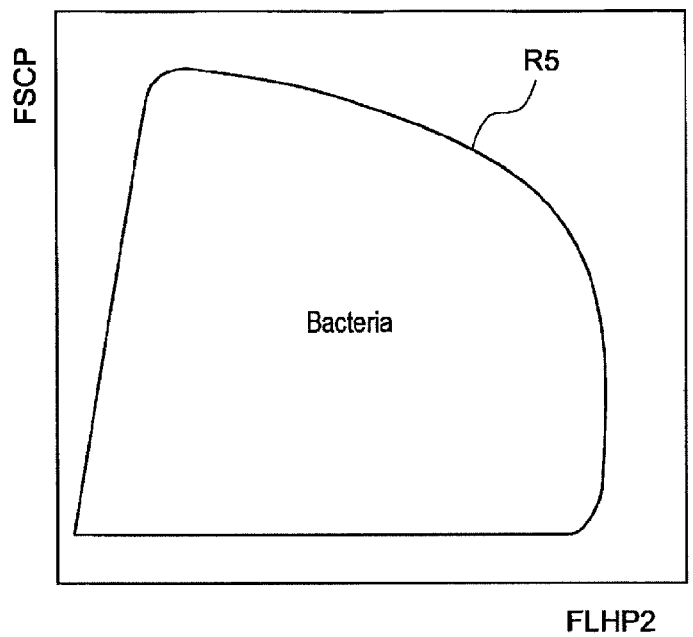
FIG. 20 is a diagram showing a distribution of bacteria in a fluorescence intensity-forward scattered light intensity region.

In the bacteria detection processing S405, bacteria are detected using the FSC and FLH2 obtained by measuring the second measurement sample, and the number thereof is counted. A bacterium has a significantly smaller size and a smaller nucleic acid amount than any other nucleated cell such as a white blood cell, and therefore has a very small fluorescence amount. Accordingly, bacteria are detected using FLH2. FIG. 20 is a diagram showing a distribution of bacteria in FLHP2-FSCP space. In the diagram, the horizontal axis indicates FLHP2, and the vertical axis indicates FSCP. As shown in the diagram, bacteria appear in a predetermined region R5. Other nucleated cells such as white blood cells (not shown) appear in a region having a fluorescence intensity higher than that of the region R5. Furthermore, impurities not having nucleic acids (not shown) appear in a region having a fluorescence intensity lower than that of the region R5. In the bacteria detection processing, particles contained in the region R5 shown in the diagram are detected as bacteria, and the number thereof is counted.

Figure 21:
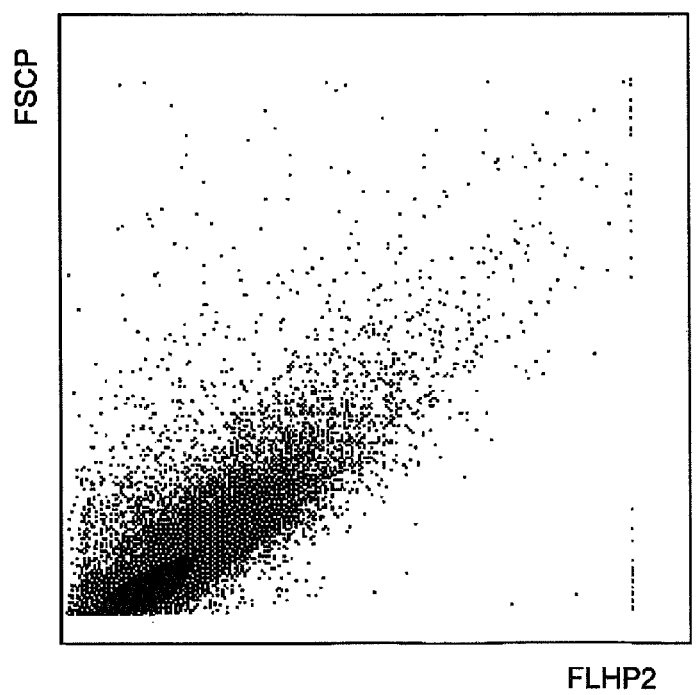
FIG. 21 is a scattergram showing an exemplary detection result of bacteria.

FIG. 21 shows a specific detection result in the bacteria detection processing S405. FIG. 21 is a scattergram showing an exemplary detection result of bacteria. FIG. 21 shows a result obtained by measuring a specimen containing bacteria.

If the measurement data analysis processing ends, the CPU 401 returns the procedure to the main routine.

The CPU 401 displays an analysis result obtained by this measurement data analysis processing, on the display portion 409 (Step S110), and ends the procedure.

Other Embodiments

Although the foregoing embodiment described, as an example, a configuration in which red blood cells, casts, crystals, and mucus threads are detected from the first measurement sample, the present invention is not limited to this. Any configuration is possible as long as at least red blood cells are detected as particles not having nucleic acids. In addition to red blood cells, casts, crystals, or mucus threads may be optionally detected.

Although the foregoing embodiment described a configuration in which white blood cells, epithelial cells, atypical cells, sperm, *Trichomonas vaginalis*, fungi, and bacteria are detected from the second measurement sample, the present invention is not limited to this. Any configuration is possible as long as at least white blood cells are detected as cells having nucleic acids. In addition to white blood cells, epithelial cells, atypical cells, sperm, *Trichomonas vaginalis*, fungi, or bacteria may be optionally detected.

Although the foregoing embodiment described a configuration in which fluorescence signals at three sensitivities consisting of FLL, FLH1, and FLH2 are obtained from the second measurement sample, and are used to classify cells having nucleic acids into white blood cells, epithelial cells, atypical cells, sperm, *Trichomonas vaginalis*, fungi, and bacteria, the present invention is not limited to this. A configuration is possible in which fluorescence signals at two types of sensitivities are obtained and are used to classify cells having nucleic acids into a plurality of types, or in which one fluorescence signal is used to classify cells having nucleic acids into a plurality of types.

Although the foregoing embodiment described a configuration in which fluorescence signals at a plurality of sensitivities are obtained by switching both of the sensitivity of the fluorescence receiving portion 59 and the amplification factor of the amplifier circuit 50, the present invention is not limited to this. For example, a configuration is possible in which fluorescence signals at a plurality of sensitivities are obtained by switching the sensitivity of the fluorescence receiving portion 59 without switching the amplification factor of the amplifier circuit 50, or in which fluorescence signals at a plurality of sensitivities are obtained by switching the amplification factor of the amplifier circuit 50 without switching the sensitivity of the fluorescence receiving portion 59.

Although the foregoing embodiment showed an example in which the staining solution and the diluting solution are separate solutions, they may be combined into one solution.

Although the foregoing embodiment described a configuration in which the specimen drawing portion 1 sucks a predetermined amount of specimen by pipetting, and distributes specimen aliquots to the reaction tank 2u and the reaction tank 2b, the present invention is not limited to this. A configuration is possible in which a predetermined amount of specimen is taken out through a sampling valve from a sucked specimen, and aliquots each in that predetermined amount are supplied to the reaction tank 2u and the reaction tank 2b.

Although the foregoing embodiment described a configuration in which the measurement sample preparation processing, the non-nucleated component measurement processing, the nucleated component measurement processing, and the measurement data analysis processing are performed in this order, this order is merely an example, and the processing may be performed in other orders. For example, a configuration is possible in which after the first measurement sample is prepared, the non-nucleated component measurement processing is performed, and, then, the first non-nucleated component classification processing and the second non-nucleated component classification processing are performed, after which the second measurement sample is prepared, and the nucleated component measurement processing is performed, and, then, the first nucleated component classification processing, the second nucleated component classification processing, and the bacteria detection processing are performed. Furthermore, the order in which the measurement of the second measurement sample using the second set value and the measurement of the second measurement sample using the third set value in the nucleated component measurement processing also can be changed.

Although the foregoing embodiment described a configuration in which the information processing portion 13 analyzes the measurement data, the present invention is not limited to this. A configuration is also possible in which the microcomputer 11 of the measurement unit 10 analyzes the measurement data.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A urine specimen analysis device, comprising:
   a specimen drawing portion configured to draw a first aliquot and a second aliquot from a urine specimen;
   a sample preparing portion configured to prepare a first measurement sample by mixing the first aliquot and a first staining dye that stains red blood cells, and prepare a second measurement sample by mixing the second aliquot and a second staining dye that stains nucleic acids;
   a measurement portion configured to measure fluorescence emitted from the first measurement sample prepared by the sample preparing portion, and measure fluorescence emitted from the second measurement sample prepared by the sample preparing portion; and
   an information processing portion configured to detect at least red blood cells contained in the first measurement sample based on the fluorescence of the first measurement sample measured by the measurement portion, and detect at least white blood cells contained in the second measurement sample based on the fluorescence of the second measurement sample measured by the measurement portion.

2. The urine specimen analysis device according to claim 1, wherein the sample preparing portion is configured to prepare the first measurement sample without hemolyzing red blood cells contained in the first aliquot, and prepare the second measurement sample while hemolyzing red blood cells contained in the second aliquot.

3. The urine specimen analysis device according to claim 1, wherein the information processing portion is configured to distinguishably detect red blood cells and other in-urine particles not containing nucleic acids contained in the first measurement sample, based on the fluorescence of the first measurement sample.

4. The urine specimen analysis device according to claim 1, wherein the information processing portion is configured to distinguishably detect white blood cells and other in-urine particles containing nucleic acids contained in the second measurement sample, based on the fluorescence of the second measurement sample.

5. The urine specimen analysis device according to claim 1, wherein the measurement portion includes:
   a flow cell through which a measurement sample flows;
   a light source configured to emit light on the measurement sample that flows through the flow cell;
   a fluorescence receiving portion configured to receive fluorescence emitted from the measurement sample, and output a fluorescence signal; and
   a scattered light receiving portion configured to receive scattered light emitted from the measurement sample, and output a scattered light signal.

6. The urine specimen analysis device according to claim 5, wherein the measurement portion is configured to amplify, at a plurality of sensitivities, the fluorescence signal obtained from the second measurement sample, and the information processing portion is configured to detect white blood cells contained in the second measurement sample, based on the fluorescence signal amplified at a sensitivity, and detect in-urine particles which has nucleic acids and are smaller than white blood cells contained in the second measurement sample, based on the fluorescence signal amplified at a different sensitivity higher than the sensitivity for the white blood cells.

7. The urine specimen analysis device according to claim 6, wherein the plurality of sensitivities include at least a first sensitivity, a second sensitivity higher than the first sensitivity, and a third sensitivity higher than the first and second sensitivities, and the information processing portion is configured to:
   detect white blood cells contained in the second measurement sample based on a first fluorescence signal amplified at the first sensitivity;
   detect sperm or fungi contained in the second measurement sample based on a second fluorescence signal amplified at the second sensitivity; and
   detect bacteria contained in the second measurement sample based on a third fluorescence signal amplified at the third sensitivity.

8. The urine specimen analysis device according to claim 7, wherein the measurement portion is configured to obtain the first and second fluorescence signals from the second measurement sample that flows through the flow cell during a first period, and obtain the third fluorescence signal from the second measurement sample that flows through the flow cell during a second period different from the first period.

9. The urine specimen analysis device according to claim 7, wherein the information processing portion is configured to distinguish between white blood cells and epithelial cells contained in the second measurement sample based on the first fluorescence signal, and distinguish between sperm and fungi contained in the second measurement sample based on the second fluorescence signal.

10. The urine specimen analysis device according to claim 7, wherein the information processing portion is configured to:
    obtain at least a fluorescence pulse area from the first fluorescence signal;
    obtain at least a scattered light pulse width from the scattered light signal obtained from the second measurement sample; and
    classify, among particles in the second measurement sample, particles belonging to a third range determined by the fluorescence pulse area of the first fluorescence signal and the scattered light pulse width as white blood cells.

11. The urine specimen analysis device according to claim 10, wherein the information processing portion is configured to classify, among particles in the second measurement sample, particles belonging to a fourth range determined by the fluorescence pulse area of the first fluorescence signal and the scattered light pulse width as epithelial cells.

12. The urine specimen analysis device according to claim 7, wherein the information processing portion is configured to:
    obtain at least a fluorescence intensity from the second fluorescence signal;
    obtain at least a scattered light pulse width from the scattered light signal obtained from the second measurement sample; and
    classify, among particles in the second measurement sample, particles belonging to a fifth range determined by the fluorescence intensity of the second fluorescence signal and the scattered light pulse width as sperm.

13. The urine specimen analysis device according to claim 12, wherein the information processing portion classifies, among particles in the second measurement sample, particles belonging to a sixth range determined by the fluorescence intensity of the second fluorescence signal and the scattered light pulse width as fungi.

14. The urine specimen analysis device according to claim 12, wherein the information processing portion is configured to:
   obtain at least a fluorescence intensity from the third fluorescence signal;
   obtain at least a scattered light intensity from the scattered light signal obtained from the second measurement sample; and
   classify, among particles in the second measurement sample, particles belonging to a seventh range determined by the fluorescence intensity of the third fluorescence signal and the scattered light intensity as bacteria.

15. The urine specimen analysis device according to claim 5, wherein the information processing portion is configured to classify in-urine particles contained in the first measurement sample into red blood cells and other in-urine particles not containing nucleic acids, based on the fluorescence signal and the scattered light signal obtained from the first measurement sample.

16. The urine specimen analysis device according to claim 15, wherein the information processing portion is configured to distinguishably detect red blood cells and casts contained in the first measurement sample, based on the fluorescence signal and the scattered light signal obtained from the first measurement sample.

17. The urine specimen analysis device according to claim 5, wherein the information processing portion is configured to distinguishably detect white blood cells and epithelial cells contained in the second measurement sample, based on the fluorescence signal and the scattered light signal obtained from the second measurement sample.

18. The urine specimen analysis device according to claim 5, wherein the information processing portion is configured to:
   obtain at least a fluorescence intensity from the fluorescence signal obtained from the first measurement sample;
   obtain at least a scattered light intensity from the scattered light signal obtained from the first measurement sample; and
   classify, among particles in the first measurement sample, particles belonging to a first range determined by the fluorescence intensity and the scattered light intensity as red blood cells.

19. The urine specimen analysis device according to claim 5, wherein the information processing portion is configured to:
   obtain at least a fluorescence pulse area and a fluorescence pulse width from the fluorescence signal obtained from the first measurement sample; and
   classify, among particles in the first measurement sample, particles belonging to a second range determined by the fluorescence pulse area and the fluorescence pulse width as casts.

20. A urine specimen analysis method, comprising:
   distributing a urine sample to a first aliquot and a second aliquot;
   preparing a first measurement sample by mixing the first aliquot and a first staining dye that stains red blood cells;
   measuring first fluorescence emitted from the prepared first measurement sample;
   detecting at least red blood cells contained in the first measurement sample based on the measured first fluorescence;
   preparing a second measurement sample by mixing the second aliquot and a second staining dye that stains nucleic acids;
   measuring second fluorescence emitted from the prepared second measurement sample; and
   detecting at least white blood cells contained in the second measurement sample based on the measured second fluorescence.

* * * * *